(12) United States Patent
Allawi et al.

(10) Patent No.: US 10,465,248 B2
(45) Date of Patent: *Nov. 5, 2019

(54) METHOD OF CHARACTERIZING ZDHHC1 DNA

(71) Applicant: EXACT SCIENCES DEVELOPMENT COMPANY, LLC, Madison, WI (US)

(72) Inventors: Hatim T. Allawi, Middleton, WI (US); Graham P. Lidgard, Middleton, WI (US)

(73) Assignee: EXACT SCIENCES DEVELOPMENT COMPANY, LLC, Madison, WI (US)

(*) Notice: Subject to any disclaimer, the term of this patent is extended or adjusted under 35 U.S.C. 154(b) by 425 days.

This patent is subject to a terminal disclaimer.

(21) Appl. No.: 14/966,617

(22) Filed: Dec. 11, 2015

(65) Prior Publication Data

US 2016/0194721 A1    Jul. 7, 2016

Related U.S. Application Data

(60) Provisional application No. 62/091,069, filed on Dec. 12, 2014.

(51) Int. Cl.
   *C12Q 1/6886* (2018.01)
   *C12Q 1/6881* (2018.01)

(52) U.S. Cl.
   CPC ......... *C12Q 1/6886* (2013.01); *C12Q 1/6881* (2013.01); *C12Q 2600/112* (2013.01); *C12Q 2600/118* (2013.01); *C12Q 2600/154* (2013.01); *C12Q 2600/158* (2013.01)

(58) Field of Classification Search
   None
   See application file for complete search history.

(56) References Cited

U.S. PATENT DOCUMENTS

| | | |
|---|---|---|
| 4,458,066 A | 7/1984 | Caruthers et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,508,169 A | 4/1996 | Deugau et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,872,816 B1 | 3/2005 | Hall et al. |
| 7,662,594 B2 | 2/2010 | Kong et al. |
| 8,361,720 B2 | 1/2013 | Oldham-Haltom et al. |
| 8,715,937 B2 | 5/2014 | Zou et al. |
| 8,916,344 B2 | 12/2014 | Zou et al. |
| 9,000,146 B2 | 4/2015 | Bruinsma et al. |
| 9,127,318 B2 | 9/2015 | Oldham-Haltom et al. |
| 10,011,878 B2 | 7/2018 | Allawi et al. |
| 2004/0234960 A1 | 11/2004 | Olek et al. |

(Continued)

FOREIGN PATENT DOCUMENTS

| | | |
|---|---|---|
| WO | WO2005/023091 | 3/2005 |
| WO | WO2005/038051 | 4/2005 |

(Continued)

OTHER PUBLICATIONS

Vinayanuwattikun (Journal of Thoracic Oncology vol. 6 No. 11 Nov. 2011 pp. 1818-1824).*
Zou (Clinical Chemistry 58:2 375-383 2012).*
Lin (Neoplasia vol. 15 No. 4 Apr. 2013 pp. 373-383).*
Zou et al., Quantification of methylated markers with a multiplex methylation-specific technology. Clin Chem. Feb. 2012;58(2):375-83.
Alix-Panabieres et al., Circulating Tumor Cells and Circulating Tumor DNA, Ann. Rev. Med., 2012, 63:199-215.
Ballabio, et al., "Screening for steroid sulfatase (STS) gene deletions by multiplex DNA amplification," Human Genetics, 1990, 84(6): 571-573.
Barnay, "Genetic disease detection and DNA amplification using cloned thermostable ligase," Proc. Natl. Acad. Sci USA, 1991, 88:189-93.

(Continued)

*Primary Examiner* — Amanda Haney
(74) *Attorney, Agent, or Firm* — Casimir Jones, S.C.; Mary Ann D. Brow

(57) ABSTRACT

Provided herein is technology relating compositions and methods for detecting tissue cell-specific DNA, such as epithelial cell-specific DNA, in blood or blood products from a subject. The technology also relates to use of tissue cell-specific DNAs as internal controls for methylation assays.

11 Claims, 16 Drawing Sheets

Specification includes a Sequence Listing.

(56) References Cited

U.S. PATENT DOCUMENTS

| | | | |
|---|---|---|---|
| 2005/0064401 A1* | 3/2005 | Olek | C07K 14/4703 435/6.12 |
| 2007/0202525 A1 | 8/2007 | Quake et al. | |
| 2009/0191548 A1 | 7/2009 | Berlin et al. | |
| 2009/0253142 A1 | 10/2009 | Allawi et al. | |
| 2013/0012410 A1 | 1/2013 | Zou et al. | |
| 2013/0022974 A1* | 1/2013 | Chinnaiyan | C12Q 1/6886 435/6.11 |
| 2013/0084287 A1 | 4/2013 | Shames et al. | |
| 2013/0129668 A1 | 5/2013 | Firestein et al. | |
| 2014/0274748 A1 | 9/2014 | Ahlquist et al. | |
| 2015/0086567 A1 | 3/2015 | Gonsky et al. | |
| 2016/0168643 A1 | 6/2016 | Ahlquist et al. | |
| 2016/0168648 A1 | 6/2016 | Allawi et al. | |

FOREIGN PATENT DOCUMENTS

| | | |
|---|---|---|
| WO | WO2010/145796 | 12/2010 |
| WO | WO2012/155072 | 11/2012 |
| WO | WO2013/116375 | 8/2013 |
| WO | WO2016/094813 | 6/2016 |
| WO | WO2016/094839 | 6/2016 |

OTHER PUBLICATIONS

Beaucage et al., "Deoxynucleoside phosphoramidites—A new class of key intermediates for deoxypolynucleotide synthesis," Tetrahedron Lett., 1981, 22: 1859-1862.

Brown et al., "Chemical synthesis and cloning of a tyrosine tRNA gene," Meth Enzymol., 1979, 68:109-151.

Bustin, "Absolute quantification of mRNA using real-time reverse transcription polymerase chain reaction assays," J. Molecular Endocrinology, 2000, 25:169-193.

Carmona et al., DNA methylation biomarkers for noninvasive diagnosis of colorectal cancer, Cancer Prev Res (Phila). Jul. 2013;6(7):656-65.

Chamberlain et al., "Deletion screening of the Duchenne muscular dystrophy locus via multiplex DNA amplification," Nucleic Acids Research, 1988, 16(23):11141-11156.

Diehl et al., Circulating mutant DNA to assess tumor dynamics, Nat Med., 2008, 14:985-990.

Don et al., "'Touchdown' PCR to circumvent spurious priming during gene amplification," Nucleic Acids Research, 1991, 19(14):4008.

Elshimali et al., The Clinical Utilization of Circulating Cell Free DNA (CCFDNA) in Blood of Cancer Patients, Int J Mol Sci., 2013, 14:18925-18958.

Frommer et al., A genomic sequencing protocol that yields a positive display of 5-methylcytosine residues in individual DNA strands, Proc. Natl. Acad. Sci. USA, 1992, 89: 1827-31.

Guilfoyle et al., "Ligation-mediated PCR amplification of specific fragments from a class-II restriction endonuclease total digest," Nucleic Acids Research, 1997, 25:1854-1858.

Haber et al., Blood-Based Analyses of Cancer: Circulating Tumor Cells and Circulating Tumor DNA, Cancer Discovery, 2014, 4:650-661.

Hall et al., "Sensitive detection of DNA polymorphisms by the serial invasive signal amplification reaction," PNAS, 2000, 97:8272.

Hayden et al., "Multiplex-Ready PCR: A new method for multiplexed SSR and SNP genotyping," BMC Genomics, 2008, 9:80.

Hecker et al., "High and low annealing temperatures increase both specificity and yield in touchdown and stepdown PCR," Biotechniques, 1996, 20(3):478-485.

Herman et al., "Methylation-specific PCR: a novel PCR assay for methylation status of CpG islands," PNAS, 1996, 93(13):9821-9826.

Higuchi et al., "A general method of in vitro preparation and specific mutagenesis of DNA fragments: study of protein and DNA interactions," Nucleic Acids Research, 1988, 16(15):7351-7367.

Higuchi et al.,"Kinetic PCR analysis: real-time monitoring of DNA amplification reactions," Biotechnology, 1993, 11:1026-1030.

Higuchi et al., "Simultaneous amplification and detection of specific DNA sequences," Biotechnology, 1992, 10:413-417.

Kalinina et al., "Nanoliter scale PCR with TaqMan detection," Nucleic Acids Research, 1997, 25:1999-2004.

Laird, Principles and challenges of genome-wide DNA methylation analysis, Nat Rev Genet, 2010, 11: 191-203.

Lin et al., Epigenomic Alterations in Localized and Advanced Prostate Cancer, Neoplasia, 2013, 15:373-383.

Lyamichev et al.,Polymorphism identification and quantitative detection of genomic DNA by invasive cleavage of oligonucleotide probes, Nat. Biotech., 1999, 17:292-296.

Matteucci et al., "Synthesis of deoxyoligonucleotides on a polymer support," J Am Chem Soc., 1981, 103:3185-3191.

Narang et al., "Improved phosphotriester method for the synthesis of gene fragments," Meth Enzymol., 1979, 68: 90-98.

Pisetsky et al., The Blood Nucleome in Pathogenesis of SLE, Autoimmun Rev, 2010, 10:35-37.

Ring et al., Detection of circulating epithelial cells in the blood of patients with breast cancer: comparison of three techniques, Br J Cancer, 2005, 92:906-912.

Roux, "Using mismatched primer-template pairs in touchdown PCR," Biotechniques, 1994, 16(5):812-814.

Schouten et al., "Relative quantification of 40 nucleic acid sequences by multiplex ligation-dependent probe amplification," Nucleic Acids Research, 2002, 30(12): e57.

Schwarzenbach et al., Cell-free nucleic acids as biomarkers in cancer patients, Nat Rev Cancer, 2011, 11:426-437.

Triglia et al., "A procedure for in vitro amplification of DNA segments that lie outside the boundaries of known sequences," Nucleic Acids Res., 1988, 16:8186.

Vogelstein et al., "Digital PCR," PNAS, 1999, 96: 9236-41.

Zou et al, Highly methylated genes in colorectal neoplasia: implications for screening, Cancer Epidemiol Biomarkers Prev, 2007, 16: 2686-96.

International Search Report and Written Opinion for PCT/US2015/065272, dated Feb. 26, 2016, 16 pages.

International Search Report and Written Opinion for PCT/US2015/065334, dated Jul. 1, 2016, 14 pages.

Illumina Data Sheet: Epigenetics, InfinumTM HumanMehylation450 BeadChip, Mar. 9, 2012, 4 pages.

Go et al., Non-invasive aneuploidy detection using free fetal DNA and RNA in maternal plasma: recent progress and future possibilities. Hum Reprod Update. May-Jun. 2011;17(3):372-82.

Husseiny et al., Tissue-specific methylation of human insulin gene and PCR assay for monitoring beta cell death. PLoS One. Apr. 10, 2014;9(4):e94591.

Jin et al., Circulating Methylated DNA as Biomarkers for Cancer Detection. In Mehtylation—From DNA, RNA and Histones to Diseases and Treatment. 2013. Chapter 6, pp. 137-151.

Kisiel et al., 185 Novel Stool DNA Markers for Inflammatory Bowel Disease Associated Colorectal Cancer and High Grade Dysplasia: High Specificity Across Three Independent International Populations. Gastroenterology. Apr. 2016;150(4 Suppl 1):S48.

Ren et al., An Analysis of Chromosome 8 and 20 Copy Number Changes to Assist Identification of Circulating Tumor Cells in Peripheral Blood of Esophageal Carcinoma, Bulletin of Chinese Cancer, 2008, 17(6):513-517.

Strand et al., Prognostic DNA methylation markers for prostate cancer. Send to Int J Mol Sci. Sep. 18, 2014;15(9):16544-76.

Thakur et al., Double-stranded DNA in exosomes: a novel biomarker in cancer detection. Cell Research. 2014;24:766-769.

Wieczorek et al., Quantitative DNA Methylation Analysis of FOXP3 as a New Method for Counting Regulatory T Cells in Peripheral Blood and Solid Tissue, Cancer Res, 2009, 69(2):599-608.

European Supplementary Search Report for EP 15868202.1, dated Jun. 13, 2018, 9 pages.

European Supplementary Search Report for EP 15868140.31, dated Aug. 16, 2018, 12 pages.

* cited by examiner

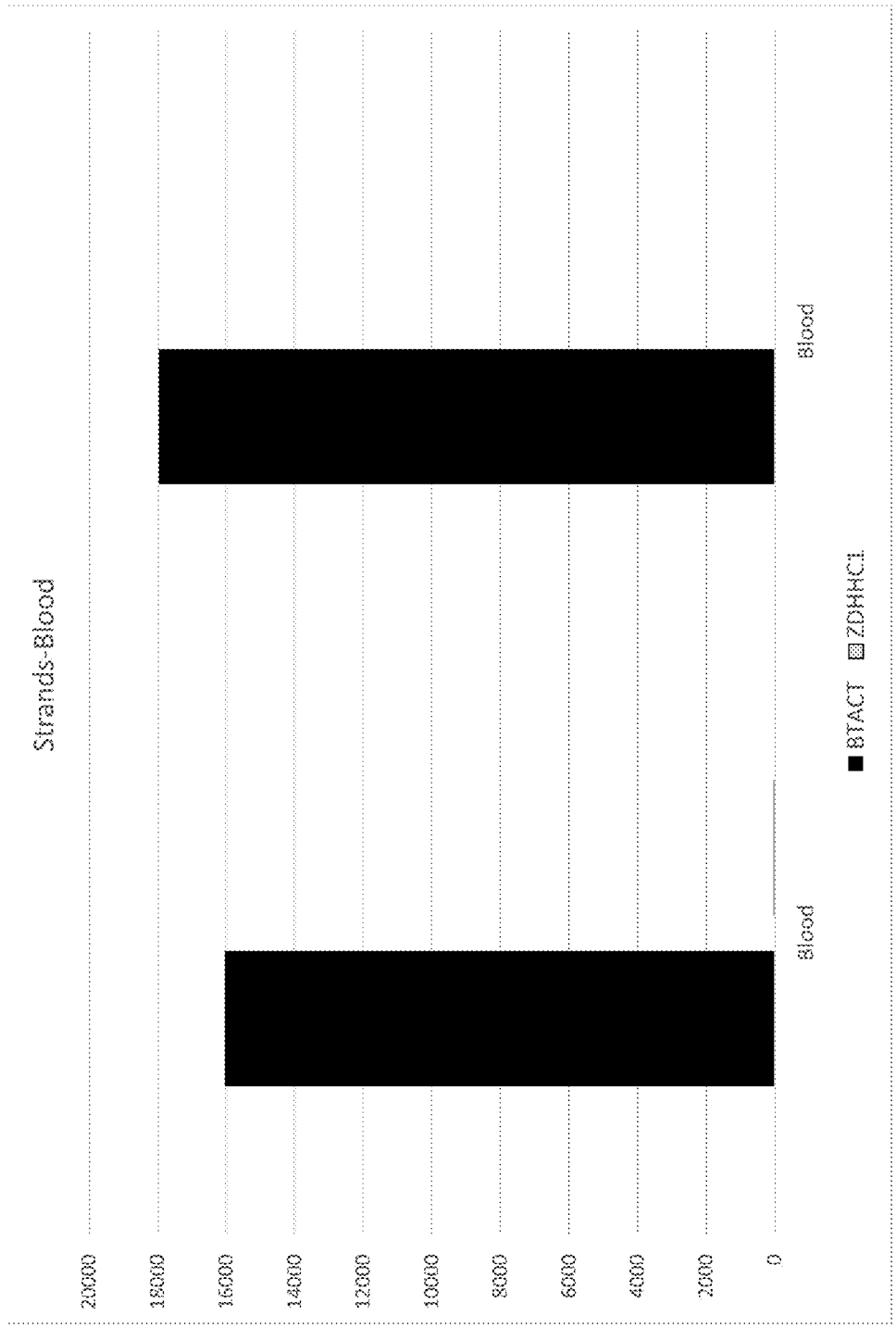

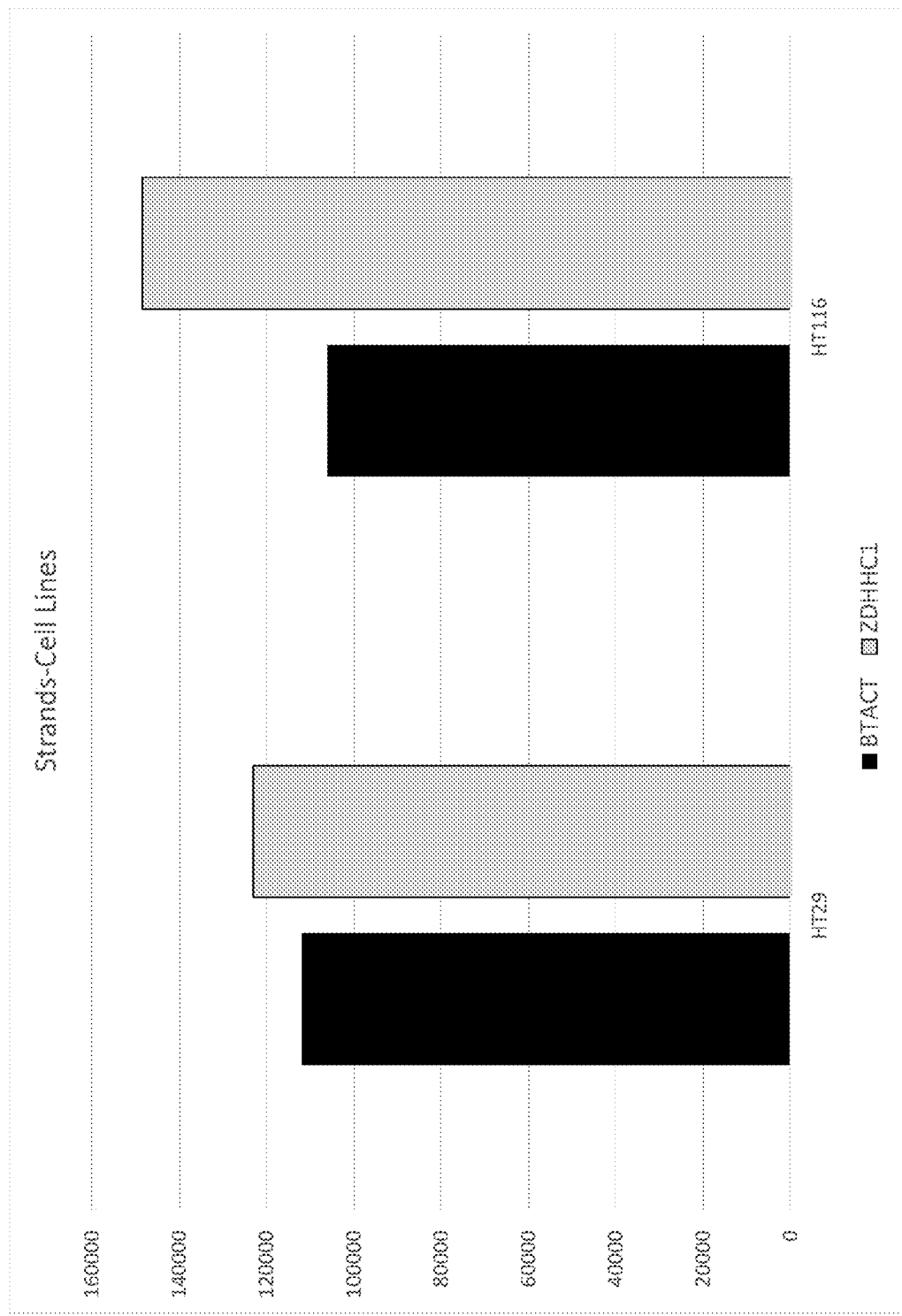

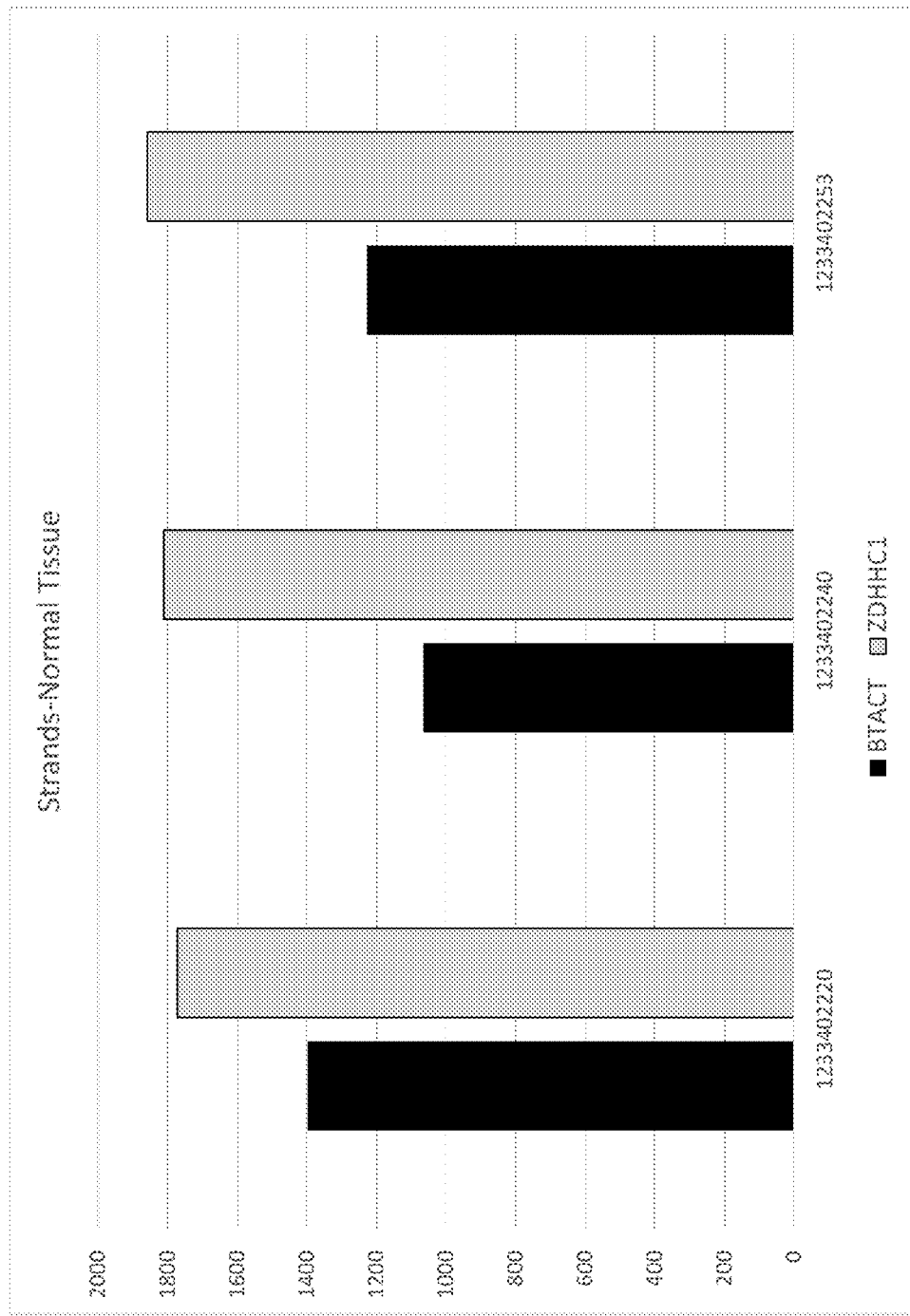

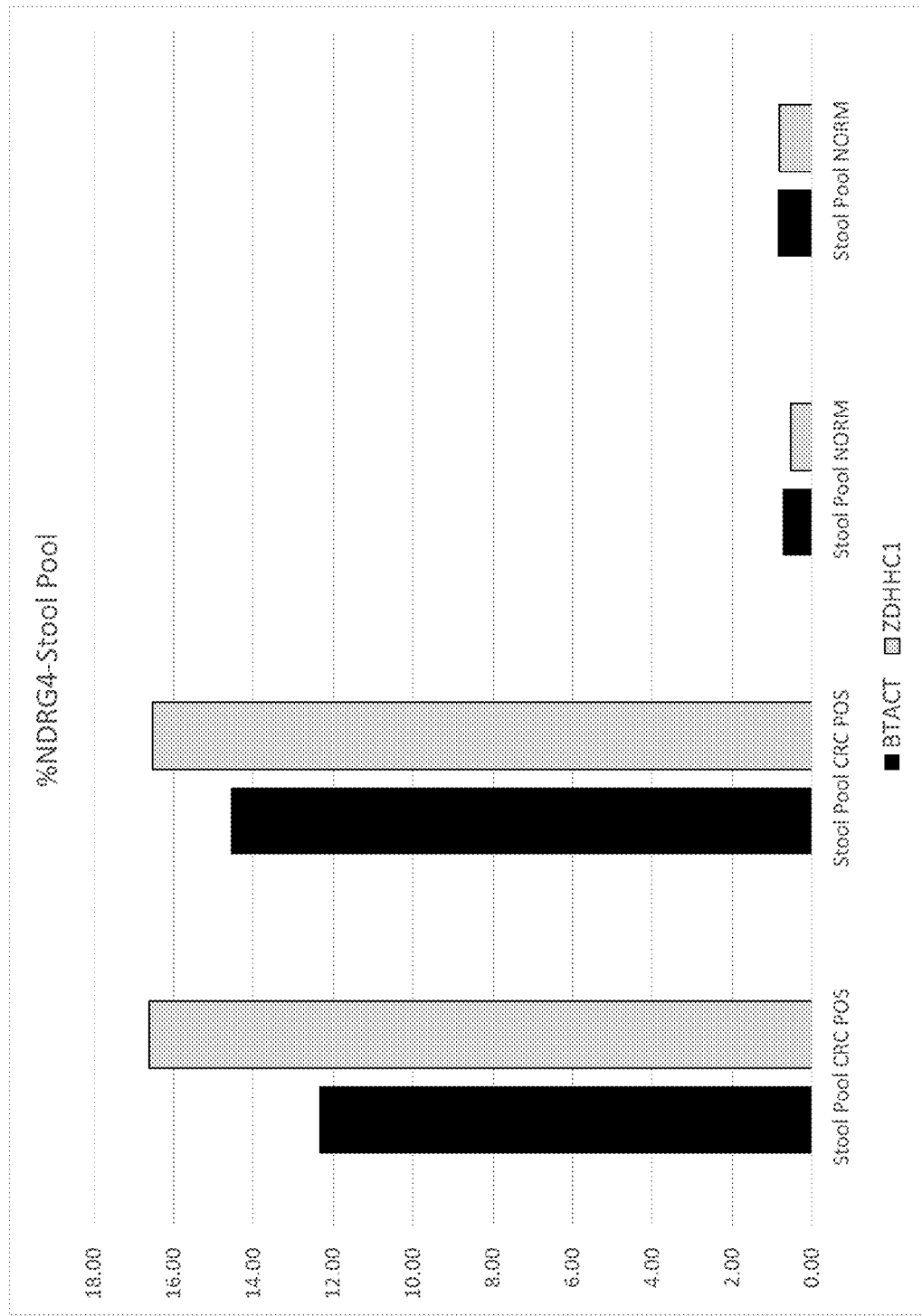

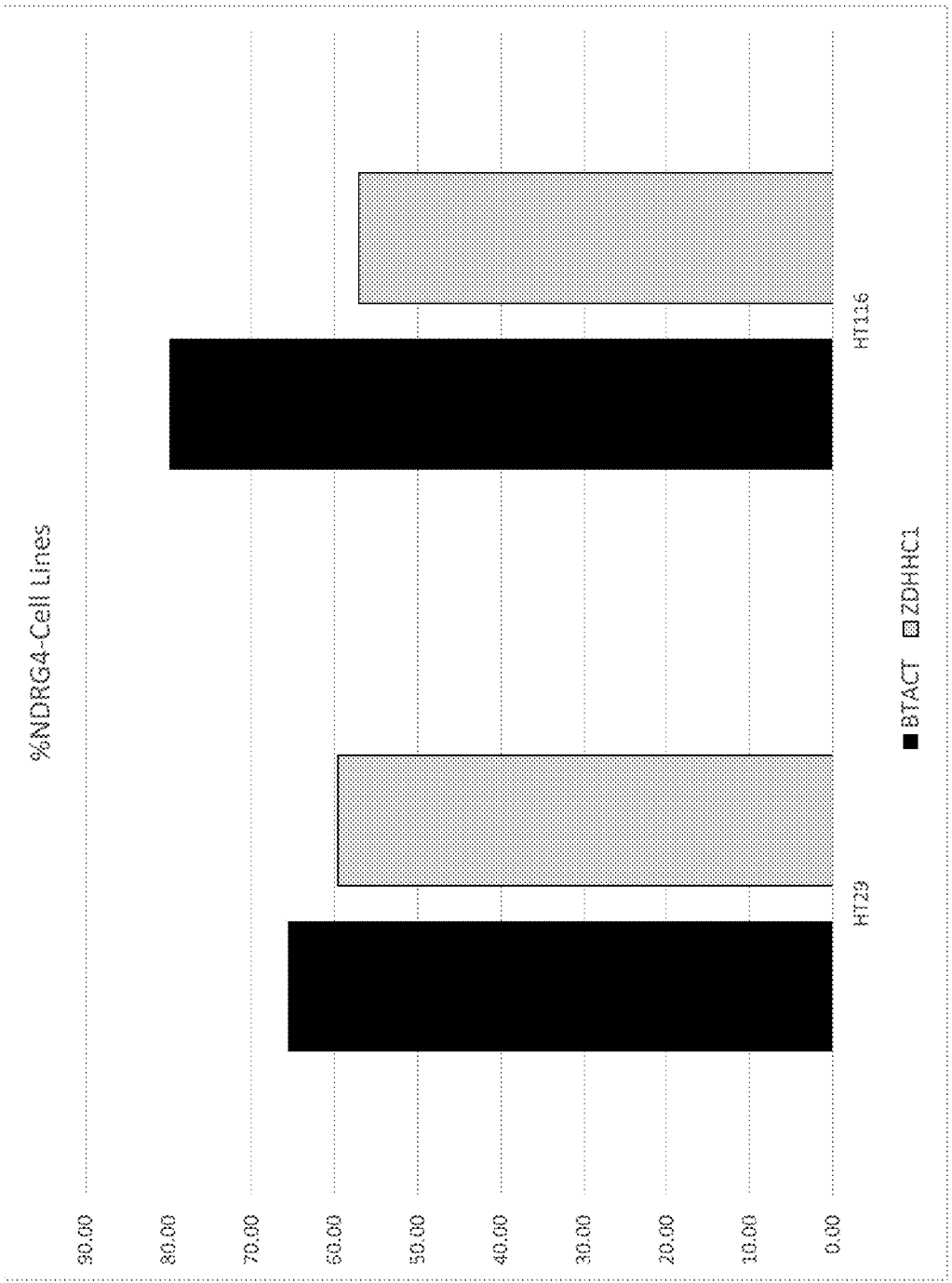

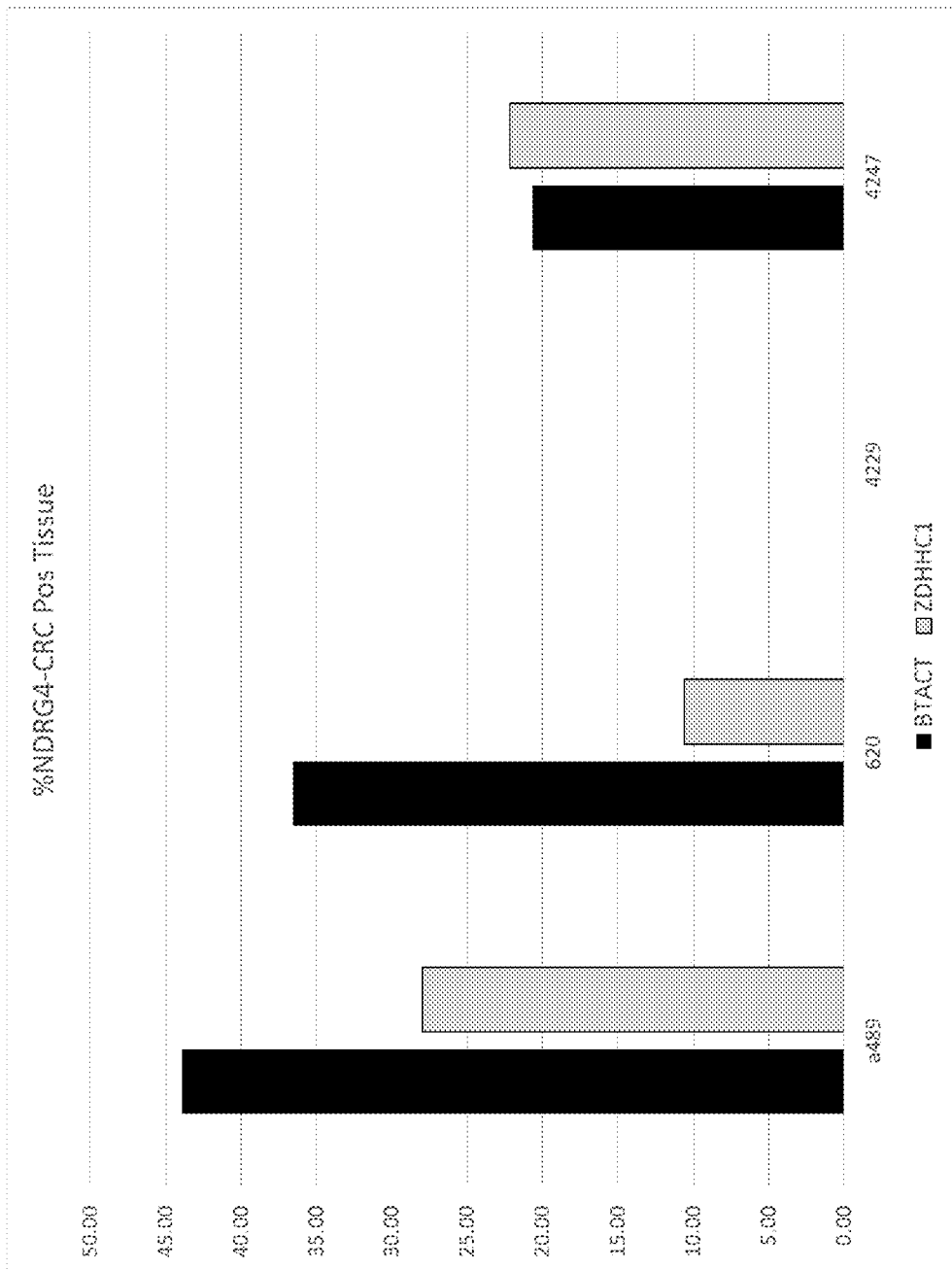

FIG. 4A

| Sample ID | Sample Type | Disease Type | Pathology | Strands ZDHHC1 Measured | Strands ZDHHC1 (Mean) |
|---|---|---|---|---|---|
| 288 | Plasma | Colorectal | Cancer | 0 | |
| 387 | Plasma | Colorectal | Cancer | 39 | |
| 388 | Plasma | Colorectal | Cancer | 0 | |
| 296 | Plasma | Colorectal | Cancer | 68 | |
| 320 | Plasma | Colorectal | Cancer | 1,291 | |
| 401 | Plasma | Colorectal | Cancer | 113 | |
| 402 | Plasma | Colorectal | Cancer | 43 | |
| 381 | Plasma | Colorectal | Cancer | 1 | |
| 297 | Plasma | Colorectal | Cancer | 283 | |
| 395 | Plasma | Colorectal | Cancer | 1,117 | |
| 321 | Plasma | Colorectal | Cancer | 21 | |
| 303 | Plasma | Colorectal | Cancer | 153 | |
| 363 | Plasma | Colorectal | Cancer | 2,427 | |
| 327 | Plasma | Colorectal | Cancer | 15 | |
| 328 | Plasma | Colorectal | Cancer | 1,006 | |
| 360 | Plasma | Colorectal | Cancer | 40 | |
| 307 | Plasma | Colorectal | Cancer | 83 | |
| 368 | Plasma | Colorectal | Cancer | 0 | |
| 393 | Plasma | Colorectal | Cancer | 1 | |
| 376 | Plasma | Colorectal | Cancer | 2,226 | |
| 316 | Plasma | Colorectal | Cancer | 35 | |
| 384 | Plasma | Colorectal | Cancer | 83 | |
| 322 | Plasma | Colorectal | Cancer | 19 | |
| 295 | Plasma | Colorectal | Cancer | 7 | |
| 300 | Plasma | Colorectal | Cancer | 2,843 | |
| 314 | Plasma | Colorectal | Cancer | 9 | 459 |

FIG. 4B

| Sample ID | Sample Type | Disease Type | Pathology | Strands ZDHHC1 Measured | Strands ZDHHC1 (Mean) |
|---|---|---|---|---|---|
| 378 | Plasma | Lung | Cancer | 2,505 | |
| 306 | Plasma | Lung | Cancer | 4 | |
| 352 | Plasma | Lung | Cancer | 4 | |
| 345 | Plasma | Lung | Cancer | 0 | |
| 339 | Plasma | Lung | Cancer | 246 | |
| 346 | Plasma | Lung | Cancer | 5 | |
| 332 | Plasma | Lung | Cancer | 10 | |
| 373 | Plasma | Lung | Cancer | 42 | |
| 315 | Plasma | Lung | Cancer | 1 | |
| 341 | Plasma | Lung | Cancer | 260 | |
| 319 | Plasma | Lung | Cancer | 223 | 300 |
| 299 | Plasma | Pancreas | Cancer | 422 | |
| 370 | Plasma | Pancreas | Cancer | 8 | |
| 382 | Plasma | Pancreas | Cancer | 73 | |
| 305 | Plasma | Pancreas | Cancer | 24 | |
| 342 | Plasma | Pancreas | Cancer | 213 | |
| 291 | Plasma | Pancreas | Cancer | 22 | |
| 333 | Plasma | Pancreas | Cancer | 0 | |
| 359 | Plasma | Pancreas | Cancer | 0 | |
| 358 | Plasma | Pancreas | Cancer | 17,671 | |
| 290 | Plasma | Pancreas | Cancer | 293 | |
| 294 | Plasma | Pancreas | Cancer | 2 | |
| 366 | Plasma | Pancreas | Cancer | 336 | |
| 335 | Plasma | Pancreas | Cancer | 463 | |
| 383 | Plasma | Pancreas | Cancer | 12 | |
| 311 | Plasma | Pancreas | Cancer | 66 | |
| 324 | Plasma | Pancreas | Cancer | 86 | |
| 396 | Plasma | Pancreas | Cancer | 4 | |
| 331 | Plasma | Pancreas | Cancer | 65 | |
| 386 | Plasma | Pancreas | Cancer | 20 | 1,041 |
| 355 | Plasma | Small bowel | Cancer | 12,001 | (12,001) |

FIG. 4C

| Sample ID | Sample Type | Disease Type | Pathology | Strands ZDHHC1 Measured | Strands ZDHHC1 (Mean) |
|---|---|---|---|---|---|
| 336 | Plasma | Colonoscopy negative | Normal | 1 | |
| 367 | Plasma | Colonoscopy negative | Normal | 9 | |
| 371 | Plasma | Colonoscopy negative | Normal | 4 | |
| 287 | Plasma | Colonoscopy negative | Normal | 10 | |
| 330 | Plasma | Colonoscopy negative | Normal | 0 | |
| 390 | Plasma | Colonoscopy negative | Normal | 0 | |
| 389 | Plasma | Colonoscopy negative | Normal | 38 | |
| 353 | Plasma | Colonoscopy negative | Normal | 0 | |
| 354 | Plasma | Colonoscopy negative | Normal | 0 | |
| 301 | Plasma | Colonoscopy negative | Normal | 2 | |
| 397 | Plasma | Colonoscopy negative | Normal | 18 | |
| 292 | Plasma | Colonoscopy negative | Normal | 0 | |
| 364 | Plasma | Colonoscopy negative | Normal | 0 | |
| 344 | Plasma | Colonoscopy negative | Normal | 2 | |
| 392 | Plasma | Colonoscopy negative | Normal | 2 | |
| 285 | Plasma | Colonoscopy negative | Normal | 15 | |
| 313 | Plasma | Colonoscopy negative | Normal | 1 | |
| 394 | Plasma | Colonoscopy negative | Normal | 2 | |
| 400 | Plasma | Colonoscopy negative | Normal | 1 | |
| 337 | Plasma | Colonoscopy negative | Normal | 0 | |
| 398 | Plasma | Colonoscopy negative | Normal | 0 | |

FIG. 4D

| Sample ID | Sample Type | Disease Type | Pathology | Strands ZDHHC1 Measured | Strands ZDHHC1 (Mean) |
|---|---|---|---|---|---|
| 380 | Plasma | Colonoscopy negative | Normal | 43 | |
| 293 | Plasma | Colonoscopy negative | Normal | 7 | |
| 318 | Plasma | Colonoscopy negative | Normal | 24 | |
| 374 | Plasma | Colonoscopy negative | Normal | 2 | |
| 340 | Plasma | Colonoscopy negative | Normal | 0 | |
| 338 | Plasma | Colonoscopy negative | Normal | 14 | |
| 323 | Plasma | Colonoscopy negative | Normal | 15 | |
| 329 | Plasma | Colonoscopy negative | Normal | 0 | |
| 302 | Plasma | Colonoscopy negative | Normal | 16 | |
| 369 | Plasma | Colonoscopy negative | Normal | 2 | |
| 350 | Plasma | Colonoscopy negative | Normal | 7 | |
| 289 | Plasma | Colonoscopy negative | Normal | 0 | |
| 347 | Plasma | Colonoscopy negative | Normal | 3 | |
| 298 | Plasma | Colonoscopy negative | Normal | 0 | |
| 308 | Plasma | Colonoscopy negative | Normal | 34 | |
| 334 | Plasma | Colonoscopy negative | Normal | 0 | |
| 361 | Plasma | Colonoscopy negative | Normal | 13 | |
| 348 | Plasma | Colonoscopy negative | Normal | 7 | |
| 349 | Plasma | Colonoscopy negative | Normal | 1 | |
| 304 | Plasma | Colonoscopy negative | Normal | 23 | |

FIG. 4E

| Sample ID | Sample Type | Disease Type | Pathology | Strands ZDHHC1 Measured | Strands ZDHHC1 (Mean) |
|---|---|---|---|---|---|
| 343 | Plasma | Colonoscopy negative | Normal | 6 | |
| 372 | Plasma | Colonoscopy negative | Normal | 5 | |
| 391 | Plasma | Colonoscopy negative | Normal | 175 | |
| 362 | Plasma | Colonoscopy negative | Normal | 59 | |
| 286 | Plasma | Colonoscopy negative | Normal | 0 | |
| 317 | Plasma | Colonoscopy negative | Normal | 0 | |
| 399 | Plasma | Colonoscopy negative | Normal | 1 | |
| 356 | Plasma | Colonoscopy negative | Normal | 15 | |
| 379 | Plasma | Colonoscopy negative | Normal | 1 | |
| 326 | Plasma | Colonoscopy negative | Normal | 0 | |
| 377 | Plasma | Colonoscopy negative | Normal | 0 | 11 |

SEQUENCE LISTING

```
<160> NUMBER OF SEQ ID NOS: 62

<210> SEQ ID NO 1
<211> LENGTH: 48
<212> TYPE: DNA
<213> ORGANISM: Artificial sequence
<220> FEATURE:
<223> OTHER INFORMATION: DNA primer/probe

<400> SEQUENCE: 1
tccctcgcgc gtggcttccg ccttctgcgc ggctggggtg cccggtgg                 48

<210> SEQ ID NO 2
<211> LENGTH: 26
<212> TYPE: DNA
<213> ORGANISM: Artificial sequence
<220> FEATURE:
<223> OTHER INFORMATION: DNA primer/probe

<400> SEQUENCE: 2
gcgggacact ccgaaggcgc aaggag                                         26

<210> SEQ ID NO 3
<211> LENGTH: 44
<212> TYPE: DNA
<213> ORGANISM: Artificial sequence
<220> FEATURE:
<223> OTHER INFORMATION: DNA primer/probe

<400> SEQUENCE: 3
ggcctgctga aaatgactga atataaactt gtggtagttg gagc                     44

<210> SEQ ID NO 4
<211> LENGTH: 46
<212> TYPE: DNA
<213> ORGANISM: Artificial sequence
<220> FEATURE:
<223> OTHER INFORMATION: DNA primer/probe

<400> SEQUENCE: 4
ctctattgtt ggatcatatt cgtccacaaa atgattctga attagc                   46

<210> SEQ ID NO 5
<211> LENGTH: 21
```

-continued

<212> TYPE: DNA
<213> ORGANISM: Artificial sequence
<220> FEATURE:
<223> OTHER INFORMATION: DNA primer/probe

<400> SEQUENCE: 5
cggttttcgt tcgtttttc g                                      21

<210> SEQ ID NO 6
<211> LENGTH: 20
<212> TYPE: DNA
<213> ORGANISM: Artificial sequence
<220> FEATURE:
<223> OTHER INFORMATION: DNA primer/probe

<400> SEQUENCE: 6
gtaacttccg ccttctacgc                                       20

<210> SEQ ID NO 7
<211> LENGTH: 18
<212> TYPE: DNA
<213> ORGANISM: Artificial sequence
<220> FEATURE:
<223> OTHER INFORMATION: DNA primer/probe

<400> SEQUENCE: 7
cgccgagggt tcgtttat                                         18

<210> SEQ ID NO 8
<211> LENGTH: 23
<212> TYPE: DNA
<213> ORGANISM: Artificial sequence
<220> FEATURE:
<223> OTHER INFORMATION: DNA primer/probe

<400> SEQUENCE: 8
gtttaatttt cggtttcgtc gtc                                   23

<210> SEQ ID NO 9
<211> LENGTH: 17
<212> TYPE: DNA
<213> ORGANISM: Artificial sequence
<220> FEATURE:
<223> OTHER INFORMATION: DNA primer/probe

<400> SEQUENCE: 9
ctcccgacgt cgctacg                                          17

<210> SEQ ID NO 10
<211> LENGTH: 20
<212> TYPE: DNA
<213> ORGANISM: Artificial sequence
<220> FEATURE:
<223> OTHER INFORMATION: DNA primer/probe

<400> SEQUENCE: 10
cgccgaggcg gttttttgcg                                       20

<210> SEQ ID NO 11
<211> LENGTH: 18
<212> TYPE: DNA
<213> ORGANISM: Artificial sequence
<220> FEATURE:
<223> OTHER INFORMATION: DNA primer/probe

<400> SEQUENCE: 11

```
cttgtggtag ttggagca                                                    18

<210> SEQ ID NO 12
<211> LENGTH: 20
<212> TYPE: DNA
<213> ORGANISM: Artificial sequence
<220> FEATURE:
<223> OTHER INFORMATION: DNA primer/probe

<400> SEQUENCE: 12
gcgcgtccag tggcgtaggc                                                  20

<210> SEQ ID NO 13
<211> LENGTH: 22
<212> TYPE: DNA
<213> ORGANISM: Artificial sequence
<220> FEATURE:
<223> OTHER INFORMATION: DNA primer/probe

<400> SEQUENCE: 13
aaacttgtgg tagttggacc tt                                               22

<210> SEQ ID NO 14
<211> LENGTH: 20
<212> TYPE: DNA
<213> ORGANISM: Artificial sequence
<220> FEATURE:
<223> OTHER INFORMATION: DNA primer/probe

<400> SEQUENCE: 14
gcgcgtcctg tggcgtaggc                                                  20

<210> SEQ ID NO 15
<211> LENGTH: 25
<212> TYPE: DNA
<213> ORGANISM: Artificial sequence
<220> FEATURE:
<223> OTHER INFORMATION: DNA primer/probe

<400> SEQUENCE: 15
tataaacttg tggtagttgg acctc                                            25

<210> SEQ ID NO 16
<211> LENGTH: 20
<212> TYPE: DNA
<213> ORGANISM: Artificial sequence
<220> FEATURE:
<223> OTHER INFORMATION: DNA primer/probe

<400> SEQUENCE: 16
gcgcgtcccg tggcgtaggc                                                  20

<210> SEQ ID NO 17
<211> LENGTH: 21
<212> TYPE: DNA
<213> ORGANISM: Artificial sequence
<220> FEATURE:
<223> OTHER INFORMATION: DNA primer/probe

<400> SEQUENCE: 17
acttgtggta gttggagctc a                                                21

<210> SEQ ID NO 18
<211> LENGTH: 20
<212> TYPE: DNA
<213> ORGANISM: Artificial sequence
```

-continued

```
<220> FEATURE:
<223> OTHER INFORMATION: DNA primer/probe

<400> SEQUENCE: 18
gcgcgtccat ggcgtaggca                                                 20

<210> SEQ ID NO 19
<211> LENGTH: 21
<212> TYPE: DNA
<213> ORGANISM: Artificial sequence
<220> FEATURE:
<223> OTHER INFORMATION: DNA primer/probe

<400> SEQUENCE: 19
acttgtggta gttggagctc t                                               21

<210> SEQ ID NO 20
<211> LENGTH: 20
<212> TYPE: DNA
<213> ORGANISM: Artificial sequence
<220> FEATURE:
<223> OTHER INFORMATION: DNA primer/probe

<400> SEQUENCE: 20
gcgcgtcctt ggcgtaggca                                                 20

<210> SEQ ID NO 21
<211> LENGTH: 22
<212> TYPE: DNA
<213> ORGANISM: Artificial sequence
<220> FEATURE:
<223> OTHER INFORMATION: DNA primer/probe

<400> SEQUENCE: 21
aacttgtggt agttggagat gc                                              22

<210> SEQ ID NO 22
<211> LENGTH: 20
<212> TYPE: DNA
<213> ORGANISM: Artificial sequence
<220> FEATURE:
<223> OTHER INFORMATION: DNA primer/probe

<400> SEQUENCE: 22
gcgcgtccct ggcgtaggca                                                 20

<210> SEQ ID NO 23
<211> LENGTH: 18
<212> TYPE: DNA
<213> ORGANISM: Artificial sequence
<220> FEATURE:
<223> OTHER INFORMATION: DNA primer/probe

<400> SEQUENCE: 23
ggtagttgga gctggtca                                                   18

<210> SEQ ID NO 24
<211> LENGTH: 20
<212> TYPE: DNA
<213> ORGANISM: Artificial sequence
<220> FEATURE:
<223> OTHER INFORMATION: DNA primer/probe

<400> SEQUENCE: 24
gcgcgtccac gtaggcaaga                                                 20
```

```
<210> SEQ ID NO 25
<211> LENGTH: 22
<212> TYPE: DNA
<213> ORGANISM: Artificial sequence
<220> FEATURE:
<223> OTHER INFORMATION: DNA primer/probe

<400> SEQUENCE: 25
ctattgttgg atcatattcg tc                                              22

<210> SEQ ID NO 26
<211> LENGTH: 70
<212> TYPE: DNA
<213> ORGANISM: Homo sapiens

<400> SEQUENCE: 26
ggggccgggg ccgacagccc acgctggcgc ggcaggcgcg tgcgcccgcc gttttcgtga    60
gcccgagcag                                                            70

<210> SEQ ID NO 27
<211> LENGTH: 70
<212> TYPE: DNA
<213> ORGANISM: Homo sapiens

<400> SEQUENCE: 27
ggggtcgggg tcgatagttt acgttggcgc ggtaggcgcg tgcgttcgtc gttttcgtga    60
gttcgagtag                                                            70

<210> SEQ ID NO 28
<211> LENGTH: 12
<212> TYPE: DNA
<213> ORGANISM: Artificial sequence
<220> FEATURE:
<223> OTHER INFORMATION: DNA primer/probe

<400> SEQUENCE: 28
gttggcgcgg ta                                                         12

<210> SEQ ID NO 29
<211> LENGTH: 20
<212> TYPE: DNA
<213> ORGANISM: Artificial sequence
<220> FEATURE:
<223> OTHER INFORMATION: DNA primer/probe

<400> SEQUENCE: 29
gtcggggtcg atagtttacg                                                 20

<210> SEQ ID NO 30
<211> LENGTH: 20
<212> TYPE: DNA
<213> ORGANISM: Artificial sequence
<220> FEATURE:
<223> OTHER INFORMATION: DNA primer/probe

<400> SEQUENCE: 30
cgaactcacg aaaacgacga                                                 20

<210> SEQ ID NO 31
<211> LENGTH: 12
<212> TYPE: DNA
<213> ORGANISM: Artificial sequence
<220> FEATURE:
<223> OTHER INFORMATION: DNA primer/probe
```

<400> SEQUENCE: 31
gacgaacgca cg                                                         12

<210> SEQ ID NO 32
<211> LENGTH: 19
<212> TYPE: DNA
<213> ORGANISM: Artificial sequence
<220> FEATURE:
<223> OTHER INFORMATION: DNA primer/probe

<400> SEQUENCE: 32
actcgaactc acgaaaacg                                                  19

<210> SEQ ID NO 33
<211> LENGTH: 70
<212> TYPE: DNA
<213> ORGANISM: Homo sapiens

<400> SEQUENCE: 33
ggggucgggg ucgauaguuu acgutggcgc gguaggcgcg tgcguucguc gttttcgtga     60
guucgaguag                                                            70

<210> SEQ ID NO 34
<211> LENGTH: 21
<212> TYPE: DNA
<213> ORGANISM: Artificial sequence
<220> FEATURE:
<223> OTHER INFORMATION: DNA primer/probe

<400> SEQUENCE: 34
gacgcggagg ttggcgcggt a                                               21

<210> SEQ ID NO 35
<211> LENGTH: 21
<212> TYPE: DNA
<213> ORGANISM: Artificial sequence
<220> FEATURE:
<223> OTHER INFORMATION: DNA primer/probe

<400> SEQUENCE: 35
gacgcggagg acgaacgcac g                                               21

<210> SEQ ID NO 36
<211> LENGTH: 28
<212> TYPE: DNA
<213> ORGANISM: Artificial sequence
<220> FEATURE:
<223> OTHER INFORMATION: DNA primer/probe

<400> SEQUENCE: 36
ctcgggctca cgaaaacggc gggcgcac                                        28

<210> SEQ ID NO 37
<211> LENGTH: 77
<212> TYPE: DNA
<213> ORGANISM: Homo sapiens

<400> SEQUENCE: 37
tctctgtgta ctaatttccc tttttggccg gacgtggtgg ctcacgcctg taatcccagc     60
actttgggag gccaaag                                                    77

<210> SEQ ID NO 38

```
<211> LENGTH: 77
<212> TYPE: DNA
<213> ORGANISM: Homo sapiens

<400> SEQUENCE: 38 ttttgtgta ttaattttt tttttggtcg gacgtggtgg tttacgtttg taatttagt      60 attttgggag gttaaag                                                  77

<210> SEQ ID NO 39
<211> LENGTH: 12
<212> TYPE: DNA
<213> ORGANISM: Artificial sequence
<220> FEATURE:
<223> OTHER INFORMATION: DNA primer/probe

<400> SEQUENCE: 39
acgtggtggt tt                                                       12

<210> SEQ ID NO 40
<211> LENGTH: 28
<212> TYPE: DNA
<213> ORGANISM: Artificial sequence
<220> FEATURE:
<223> OTHER INFORMATION: DNA primer/probe

<400> SEQUENCE: 40
tgtgtattaa ttttttttt tggtcgga                                       28

<210> SEQ ID NO 41
<211> LENGTH: 28
<212> TYPE: DNA
<213> ORGANISM: Artificial sequence
<220> FEATURE:
<223> OTHER INFORMATION: DNA primer/probe

<400> SEQUENCE: 41
cctcccaaaa tactaaaatt acaaacgt                                      28

<210> SEQ ID NO 42
<211> LENGTH: 21
<212> TYPE: DNA
<213> ORGANISM: Artificial sequence
<220> FEATURE:
<223> OTHER INFORMATION: DNA primer/probe

<400> SEQUENCE: 42
gacgcggaga cgtggtggtt t                                             21

<210> SEQ ID NO 43
<211> LENGTH: 35
<212> TYPE: DNA
<213> ORGANISM: Artificial sequence
<220> FEATURE:
<223> OTHER INFORMATION: DNA primer/probe

<400> SEQUENCE: 43
gtgctgggat tacaggcgtg agccaccacg tccgg                              35

<210> SEQ ID NO 44
<211> LENGTH: 77
<212> TYPE: DNA
<213> ORGANISM: Homo sapiens

<400> SEQUENCE: 44
ccatctatag aaaaatggat tagggccggg cacagtggct cacgcctgta atcccagcac   60
```

```
tttgggaggc cgaggca                                                       77

<210> SEQ ID NO 45
<211> LENGTH: 77
<212> TYPE: DNA
<213> ORGANISM: Homo sapiens

<400> SEQUENCE: 45
ttatttatag aaaaatggat tagggtcggg tatagtggtt tacgtttgta attttagtat        60
tttgggaggt cgaggta                                                       77

<210> SEQ ID NO 46
<211> LENGTH: 12
<212> TYPE: DNA
<213> ORGANISM: Artificial sequence
<220> FEATURE:
<223> OTHER INFORMATION: DNA primer/probe

<400> SEQUENCE: 46
aacgtaaacc ac                                                            12

<210> SEQ ID NO 47
<211> LENGTH: 22
<212> TYPE: DNA
<213> ORGANISM: Artificial sequence
<220> FEATURE:
<223> OTHER INFORMATION: DNA primer/probe

<400> SEQUENCE: 47
gaaaaatgga ttagggtcgg gt                                                 22

<210> SEQ ID NO 48
<211> LENGTH: 28
<212> TYPE: DNA
<213> ORGANISM: Artificial sequence
<220> FEATURE:
<223> OTHER INFORMATION: DNA primer/probe

<400> SEQUENCE: 48
tcgacctccc aaaatactaa aattacaa                                           28

<210> SEQ ID NO 49
<211> LENGTH: 21
<212> TYPE: DNA
<213> ORGANISM: Artificial sequence
<220> FEATURE:
<223> OTHER INFORMATION: DNA primer/probe

<400> SEQUENCE: 49
gacgcggaga acgtaaacca c                                                  21

<210> SEQ ID NO 50
<211> LENGTH: 36
<212> TYPE: DNA
<213> ORGANISM: Artificial sequence
<220> FEATURE:
<223> OTHER INFORMATION: DNA primer/probe

<400> SEQUENCE: 50
cggcctccca aagtgctggg attacaggcg tgagcc                                  36

<210> SEQ ID NO 51
<211> LENGTH: 29
<212> TYPE: DNA
```

```
<213> ORGANISM: Artificial sequence
<220> FEATURE:
<223> OTHER INFORMATION: DNA primer/probe

<400> SEQUENCE: 51
agccggtttt ccggctgaga ctccgcgtc                                29

<210> SEQ ID NO 52
<211> LENGTH: 27
<212> TYPE: DNA
<213> ORGANISM: Artificial sequence
<220> FEATURE:
<223> OTHER INFORMATION: DNA primer/probe

<400> SEQUENCE: 52 tttgttttt tgattaggtg tttaaga                                   27

<210> SEQ ID NO 53
<211> LENGTH: 0
<212> TYPE: DNA
<213> ORGANISM: Artificial sequence
<220> FEATURE:
<223> OTHER INFORMATION: DNA primer/probe

<400> SEQUENCE: 53

000

<210> SEQ ID NO 54
<211> LENGTH: 0
<212> TYPE: DNA
<213> ORGANISM: Artificial sequence
<220> FEATURE:
<223> OTHER INFORMATION: DNA primer/probe

<400> SEQUENCE: 54

000

<210> SEQ ID NO 55
<211> LENGTH: 0
<212> TYPE: DNA
<213> ORGANISM: Artificial sequence
<220> FEATURE:
<223> OTHER INFORMATION: DNA primer/probe

<400> SEQUENCE: 55

000

<210> SEQ ID NO 56
<211> LENGTH: 0
<212> TYPE: DNA
<213> ORGANISM: Artificial sequence
<220> FEATURE:
<223> OTHER INFORMATION: DNA primer/probe

<400> SEQUENCE: 56

000

<210> SEQ ID NO 57
<211> LENGTH: 0
<212> TYPE: DNA
<213> ORGANISM: Artificial sequence
<220> FEATURE:
<223> OTHER INFORMATION: DNA primer/probe

<400> SEQUENCE: 57

000
```

<210> SEQ ID NO 58
<211> LENGTH: 0
<212> TYPE: DNA
<213> ORGANISM: Artificial sequence
<220> FEATURE:
<223> OTHER INFORMATION: DNA primer/probe

<400> SEQUENCE: 58

000

<210> SEQ ID NO 59
<211> LENGTH: 21
<212> TYPE: DNA
<213> ORGANISM: Artificial sequence
<220> FEATURE:
<223> OTHER INFORMATION: DNA primer/probe

<400> SEQUENCE: 59
caccaacctc ataaccttat c                                            21

<210> SEQ ID NO 60
<211> LENGTH: 21
<212> TYPE: DNA
<213> ORGANISM: Artificial sequence
<220> FEATURE:
<223> OTHER INFORMATION: DNA primer/probe

<400> SEQUENCE: 60
ccacggacga tagtgttgtg g                                            21

<210> SEQ ID NO 61
<211> LENGTH: 166
<212> TYPE: DNA
<213> ORGANISM: Homo sapiens

<400> SEQUENCE: 61
ctctgcaggt tctatttgct ttttcccaga tgagctcttt ttctggtgtt tgtctctctg    60
actaggtgtc taagacagtg ttgtgggtgt aggtactaac actggctcgt gtgacaaggc   120
catgaggctg gtgtaaagcg gccttggagt gtgtattaag taggtg                  166

<210> SEQ ID NO 62
<211> LENGTH: 166
<212> TYPE: DNA
<213> ORGANISM: Homo sapiens

<400> SEQUENCE: 62
ttttgtaggt tttatttgtt ttttttaga tgagtttttt ttttggtgtt tgttttttg    60 attaggtgtt taagatagtg ttgtgggtgt aggtattaat attggtttgt gtgataaggt   120
tatgaggttg gtgtaaagtg gttttggagt gtgtattaag taggtg                  166

METHOD OF CHARACTERIZING ZDHHC1 DNA

The present application claims priority to U.S. Provisional Application Ser. No. 62/091,069, filed Dec. 12, 2014, which is incorporated herein by reference.

FIELD OF INVENTION

Provided herein is technology relating compositions and methods for detecting epithelial cell-specific DNA in blood or blood products from a subject, wherein the presence and amount of the epithelial cell DNA in the blood or blood product is indicative of the presence of or the magnitude of a medical condition in the subject. The technology further relates to use of tissue cell-specific DNAs, e.g., epithelial cell-specific DNA, as internal controls for methylation assays in samples such as stool or tissue samples from a subject.

BACKGROUND

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) "Principles and challenges of genome-wide DNA methylation analysis" *Nat Rev Genet* 11: 191-203). Furthermore, in other cancers like sporadic colon cancer, methylation markers offer excellent specificity and are more broadly informative and sensitive than are individual DNA mutations (Zou et al (2007) "Highly methylated genes in colorectal neoplasia: implications for screening" *Cancer Epidemiol Biomarkers Prev* 16: 2686-96).

Nucleic acids from patient samples, e.g., blood, stool, and tissue samples, that are analyzed for the presence of mutations and/or for methylation status associated with disease or risk of disease typically pass through a number of process steps during analysis. These steps may comprise, e.g., filtration, precipitation, capture, washing, elution, and/or chemical modification. For analysis of DNAs to determine methylation status, e.g., the percent methylation of a test DNA, processing typically comprises treatment with bisulfite to convert un-methylated dC bases to dU residues, making them more readily distinguishable from the methyl-C residues that are protected from bisulfite conversion.

Accurate quantitation of a test DNA (e.g., determining percent methylation, presence and amount of DNA carrying a mutation, etc.) typically requires normalization to a control nucleic acid, e.g., an endogenous invariant gene having known features (e.g., known sequence, known copy-number per cell). Normalizing controls for sample-to-sample variations that may occur in, for example, sample processing, assay efficiency, etc., and allows accurate sample-to-sample data comparison.

Cancer-specific marker DNA in blood or blood products, present either within circulating cancer cells or complexes, or as circulating cell-free DNA, has been used for characterizing solid tumors, e.g., breast carcinomas, in subjects. However, the utility of analyzing blood for particular cancer markers is limited to the assessment of particular source tumors or types of cancers that have already been characterized for those markers, and the detection of particular markers in a the blood of a subject may be of limited use in detecting other conditions or cancers.

SUMMARY

Provided herein is technology relating to characterizing samples, e.g., blood samples, stool samples, etc., for the presence or absence of, and/or the amounts of different species of nucleic acids that, for example, may be associated with a health status of a subject. For example, in some embodiments, the technology relates to detecting and measuring DNA associated with a particular tissue in a sample type that does not typically contain DNA from that tissue. In preferred embodiments, the technology is directed to detecting and/or measuring epithelial cells and/or epithelial cell-specific DNA in blood or blood product samples.

In some embodiments, the technology provides a method for monitoring a disease state in a subject, the method comprising the steps of, for example, obtaining a first blood product sample from a subject at a first time point; initiating a treatment protocol, where the treatment protocol comprises therapeutic intervention; obtaining a second blood product sample from the subject at a second time point, wherein the second time point is after initiation of said treatment protocol; and assaying the first blood product sample and the second blood product sample for an amount of an epithelial cell-specific DNA, wherein a difference in the amount of epithelial cell-specific DNA between the first blood product sample and the second blood product sample is indicative of a change in the disease state in said subject. The technology is not limited with respect to when the first and second blood product samples are assayed. For example, in some embodiments, the first blood product sample is assayed before the start of the treatment protocol, while in other embodiments, the first blood product sample is assayed during the treatment protocol, or after the treatment protocol, e.g., at the same time as the second blood product sample. In preferred embodiments, the method comprises generating a record, e.g., a patient record such a hard-copy or electronic medical record, wherein the record reports a result of the assaying, e.g., reports a value (e.g., an amount, or change in amount of epithelial call-specific DNA in comparative samples), or a diagnostic result that is based on a value.

The methods are not limited to any particular treatment protocol. In some embodiments, the treatment protocol may comprise no active intervention, e.g., it may be a matter of keeping a subject under observation. In preferred embodiments, the treatment protocol comprises one or more of surgery, drug therapy, chemotherapy, immunotherapy, nutritional therapy, radiation therapy, temperature therapy, and physical therapy.

A difference in the amount of epithelial cell-specific DNA between the first blood product sample and the second blood product sample is indicative, for example, of recurrence, progression, or regression of the disease state in said subject. In some embodiments, no treatment protocol is used after the first sample is collected, and a difference in the amount of epithelial cell-specific DNA between the first blood product sample and the second blood product sample is indicative of an initial occurrence of a disease state in the subject. In some embodiments, the disease state indicated by the presence of epithelial cell-specific DNA in blood or a blood product sample is cancer, e.g., metastatic cancer.

In some preferred embodiments, the epithelial cell-specific DNA comprises a DNA that is methylated in epithelial cells and is not methylated in blood cells. In such embodiments, a preferred method comprises treating DNA from the blood product sample(s) with a bisulfite reagent to create converted epithelial cell-specific DNA. In preferred embodiments, the epithelial cell-specific DNA comprises ZDHHC1 DNA, and in particularly preferred embodiments, the DNA comprises at least a portion of the sequence shown in SEQ ID NO:26.

The method is not limited to any particular form of blood or blood product sample, In certain preferred embodiments, the blood product is plasma.

The methods are not limited to any particular means of assaying the samples. In certain preferred embodiments, assaying comprises using polymerase chain reaction, nucleic acid sequencing, mass spectrometry, methylation-specific nuclease, mass-based separation, or DNA target capture. In particularly preferred embodiments, assaying comprises using a flap endonuclease assay.

In some embodiments, the technology provides compositions related to analyzing sample(s) from a subject. For example, in some embodiments, the composition comprises a strand of DNA comprising the nucleotide sequence of SEQ ID NO:33, and/or a strand of DNA comprising the nucleotide sequence of SEQ ID NO:27. In some embodiments, the composition further comprising a detection probe oligonucleotide, wherein the detection probe oligonucleotide comprises a region that is complementary to a portion of said strand of DNA. In preferred embodiments, the detection probe oligonucleotide comprises a region that is complementary to a portion of SEQ ID NO:27 and/or to a portion of SEQ ID NO:33. In particularly preferred embodiments, the detection probe oligonucleotide comprises a reporter molecule. The reporter molecule is not limited to any particular detectable moiety. In preferred embodiments, the reporter molecule comprises a fluorophore. In some embodiments, the detection probe comprises a flap sequence.

In certain preferred embodiments, the composition further comprises one or more of a FRET cassette oligonucleotide, flap endonuclease, e.g., a FEN-1 endonuclease, and/or a DNA polymerase, e.g., a thermostable DNA polymerase. In preferred embodiments, the DNA polymerase is a bacterial DNA polymerase. In some embodiments, the technology provides a reaction mixture, e.g., for a detection assay, comprising any combination of the compositions described above.

In some embodiments, the technology relates to performing methylation assays. In particular, in some embodiments, the technology relates to internal controls for methylation assays.

In some embodiments, the technology provides a method of characterizing a blood or blood product sample from a subject comprising assaying said sample to detect the presence of tissue cell-specific DNA, wherein the presence of the tissue cell-specific DNA is indicative of the presence of tissue cells or DNA from tissue cells in the blood or blood product sample. Tissue cell DNA may be present within tissue cells in the blood, or within other complexes (e.g., nucleosomes, episomes, immune complexes, microparticles, etc., or it may be in the form of circulating cell-free DNA (ccfDNA). In some embodiments, the tissue cell-specific DNA is epithelial cell-specific DNA. In certain preferred embodiments, the blood product sample is a plasma sample.

In some particularly preferred embodiments, the tissue cell-specific DNA is epithelial cell-specific DNA that is methylated in epithelial cells and is not methylated in blood cells, and the application of the technology preferably comprises treating DNA from the sample with a bisulfite reagent to create converted tissue cell-specific DNA. In particularly preferred embodiments, the epithelial cell-specific DNA comprises ZDHHC1 DNA, as described herein below.

The method of analyzing the tissue-cell specific DNA is not limited to any particular method of DNA analysis. In come embodiments, the assaying comprises using polymerase chain reaction, nucleic acid sequencing, mass spectrometry, methylation-specific nuclease, mass-based separation, and/or DNA target capture. In preferred embodiments, the assay comprises a flap endonuclease assay. In some preferred embodiments, the assay is a flap endonuclease assay, e.g., a QUARTS assay.

In some embodiments, the technology provides reference DNAs that are usable for determining total human DNA input in a sample, as a means of determining the relative amount of a test nucleic acid, e.g., the percentage of methylation of a cancer marker gene, in the sample. In certain preferred embodiments, the technology provides reference DNAs having methylation features similar to the marker DNAs to which they are to be compared, such that the reference DNAs can be exposed to the same preparative steps as marker DNAs, and will behave like marker DNAs.

In some embodiments, the technology provides control or marker DNAs that are specific for tissue cells, e.g., epithelial cells. In particular embodiments, the technology provides marker DNAs that are highly methylated, e.g., in tissue cells,—e.g., both normal and cancer epithelial cells—but that are not methylated in blood, e.g., in lymphocytes. These marker DNAs find numerous applications. For example, in some embodiments, these markers find use as control or reference DNAs in quantifying tissue-derived DNA in samples that may also contain blood cells such as lymphocytes that would produce background in the detection of other control DNAs, e.g., β-actin. These tissue cell-specific markers also find application in the detection of tissue cells in samples where tissue cells or tissue DNA are normally absent, e.g., in blood, wherein the presence of tissue cells or tissue DNA may indicate the presence of disease, e.g., metastasis in cancer.

For example, in some embodiments, the technology provides methods of performing a quantitative nucleic acid detection assay, comprising assaying a sample from a subject for an amount of at least one marker gene; assaying the same sample for an amount of ZDHHC1 DNA, and comparing the amount of the at least one marker gene to the amount of ZDHHC1 DNA in the sample to determine the amount of the at least one marker gene relative to the amount of ZDHHC1 DNA in said sample. In some embodiments, external controls, e.g., calibration standards may be used to determine absolute quantitation of the marker genes and/or the ZDHHC1 DNA.

In some embodiments, the technology comprises treating DNA from the sample with a bisulfate reagent to create converted ZDHHC1 DNA and at least one converted marker gene, such that assaying for an amount of a marker gene and the ZDHHC1 DNA comprises assaying an amount of converted marker gene and converted ZDHHC1 DNA.

The methods of assaying the nucleic acids recited above are not limited to any particular method. In some embodiments, the assaying comprises using one or more of polymerase chain reaction, nucleic acid sequencing, mass spectrometry, methylation specific nuclease, mass-based separation, or target capture. In some preferred embodiments, assaying of the marker DNA and assaying of the ZDHHC1 DNA are done in a single reaction. In particularly preferred embodiments, the assay is a flap endonuclease assay, e.g., a QUARTS assay.

In some embodiments, the amount of converted marker gene relative to the amount of converted ZDHHC1 DNA is indicative of a methylation state of the marker, e.g., in a test sample, and the methylation state comprises increased or decreased methylation of the marker gene relative to a normal methylation state of the marker gene. In certain preferred embodiments, an increased percent methylation is indicative of a disease state.

Further embodiments provide a method of detecting tissue cells in blood or blood product, comprising: detecting the presence of methylated ZDHHC1 in a blood or blood product sample from a subject, wherein the presence of the methylated ZDHHC1 is indicative of the presence of tissue cells, e.g., epithelial cells, in the blood. In some embodiments, the presence of tissue cells in the sample is indicative of metastatic cancer in the subject. In some embodiments, the blood product is plasma. In some embodiments, the assaying comprises using polymerase chain reaction, nucleic acid sequencing, mass spectrometry, methylation specific nuclease, mass-based separation, or target capture. In some embodiments, the assay is a flap endonuclease assay, e.g., a QUARTS assay. In some embodiments, the cancer is colorectal cancer.

Additional embodiments provide a method of detecting metastatic cancer in a blood or blood product sample from a subject, comprising: detecting the presence of methylated ZDHHC1 in a blood or blood product sample from a subject, wherein the presence of the methylated ZDHHC1 is indicative of the presence of metastatic cancer in the subject. Yet other embodiments provide a kit, comprising: a) at least one oligonucleotide, wherein at least a portion of the oligonucleotide specifically hybridizes to ZDHHC1; and b) bisulfite. In some embodiments, the oligonucleotide is selected from one or more of, for example, a capture oligonucleotide, a pair of nucleic acid primers, a nucleic acid probe, or an INVADER oligonucleotide. In some embodiments, the kit further comprises one or more nucleic acids that specifically hybridize to one or more target genes. In some embodiments, the kit further comprises a solid support (e.g. magnetic bead). In some embodiments, the solid support comprises one or more capture reagents (e.g., oligonucleotides complementary to ZDHHC1 and/or additional target genes).

Additional embodiments provide a composition, comprising: a complex of a ZDHHC1 nucleic acid and at least one oligonucleotide, wherein at least a portion of the oligonucleotide is hybridized to the ZDHHC1 nucleic acid. In some embodiments, the compositions further comprises one or more additional reaction mixtures comprising a complex of a target nucleic acid and one or more oligonucleotides that specifically hybridize to one or more target genes.

Still further embodiments provide a method of screening for a neoplasm in a sample obtained from a subject, the method comprising: a) assaying a sample from a subject for an amount of at least one methylated marker gene selected from the group consisting of vimentin, septin 9, NDRG4, and BMP3 in a sample obtained from a subject; assaying the sample for an amount of methylated ZDHHC1 DNA, and comparing the amount of the at least one methylated marker gene to the amount of methylated ZDHHC1 DNA in the sample to determine a methylation state for the at least one marker gene in the sample In some embodiments, the at least one marker is at least two, three, four, or all of the markers. In some embodiments, the assay further comprises the step of identifying a KRAS mutation score in the sample. In some embodiments, measuring of the K-ras mutation score is measured by quantitative allele-specific PCR. In some embodiments, the assay comprises detecting methylation states of ZDHHC1, BMP3, NDRG4, and identifying a KRAS mutation score in the sample. In some embodiments, the method further comprises the step of determining the presence of hemoglobin in the sample. In some embodiments, the patient has inflammatory bowel disease. In certain preferred embodiments, the sample is a stool sample, a tissue sample, a pancreatic juice sample, a pancreatic cyst fluid sample, a blood sample, or a urine sample. A neoplasm may comprise, for example, a pancreas neoplasm, a colorectal neoplasm, a bile duct neoplasm, a stomach neoplasm, an esophagus neoplasm, or an adenoma.

Some embodiments provide a kit, comprising: a) at least one oligonucleotide, wherein at least a portion of the oligonucleotide specifically hybridizes to ZDHHC1; and b) at least one additional oligonucleotide, wherein at least a portion of the oligonucleotide specifically hybridizes to marker selected from vimentin, septin 9, NDRG4, and BMP3. In some embodiments, the kit comprises at least two additional oligonucleotides. In some embodiments, the kit further comprises bisulfite. In some embodiments, the kit further comprises at least one oligonucleotide, wherein at least a portion of the oligonucleotide specifically hybridizes to KRAS. In some embodiments, the kit further comprises reagents for detecting the presence of hemoglobin in a stool sample.

Certain embodiments provide a composition, comprising: a) a complex of a ZDHHC1 nucleic acid and at least one oligonucleotide, wherein at least a portion of the oligonucleotide is hybridized to the ZDHHC1 nucleic acid; and b) a complex of a target nucleic acid selected from the group consisting of vimentin, septin 9, NDRG4, and BMP, and one or more oligonucleotides that specifically hybridize to the target nucleic acid.

BRIEF DESCRIPTION OF THE DRAWINGS

These and other features, aspects, and advantages of the present technology will become better understood with regard to the following drawings:

FIGS. 1A-1E provide graphs comparing the presence of β-actin (BTACT) and the methylated gene ZDHHC1 in bisulfite-converted DNA from stool, blood, cell lines, and tissue samples.

FIGS. 2A-2C provide graphs comparing the % methylation of marker gene NDRG4 as determined by comparison to control genes BTACT or ZDHHC1 measured in stool samples (2A), cell lines (2B) and colorectal cancer tissues samples (2C).

FIGS. 4A-4E provides a table showing the detection of the levels of the ZDHHC1 marker in plasma samples from subjects having the indicated cancers and from normal subjects.

DEFINITIONS

Figure 1A:
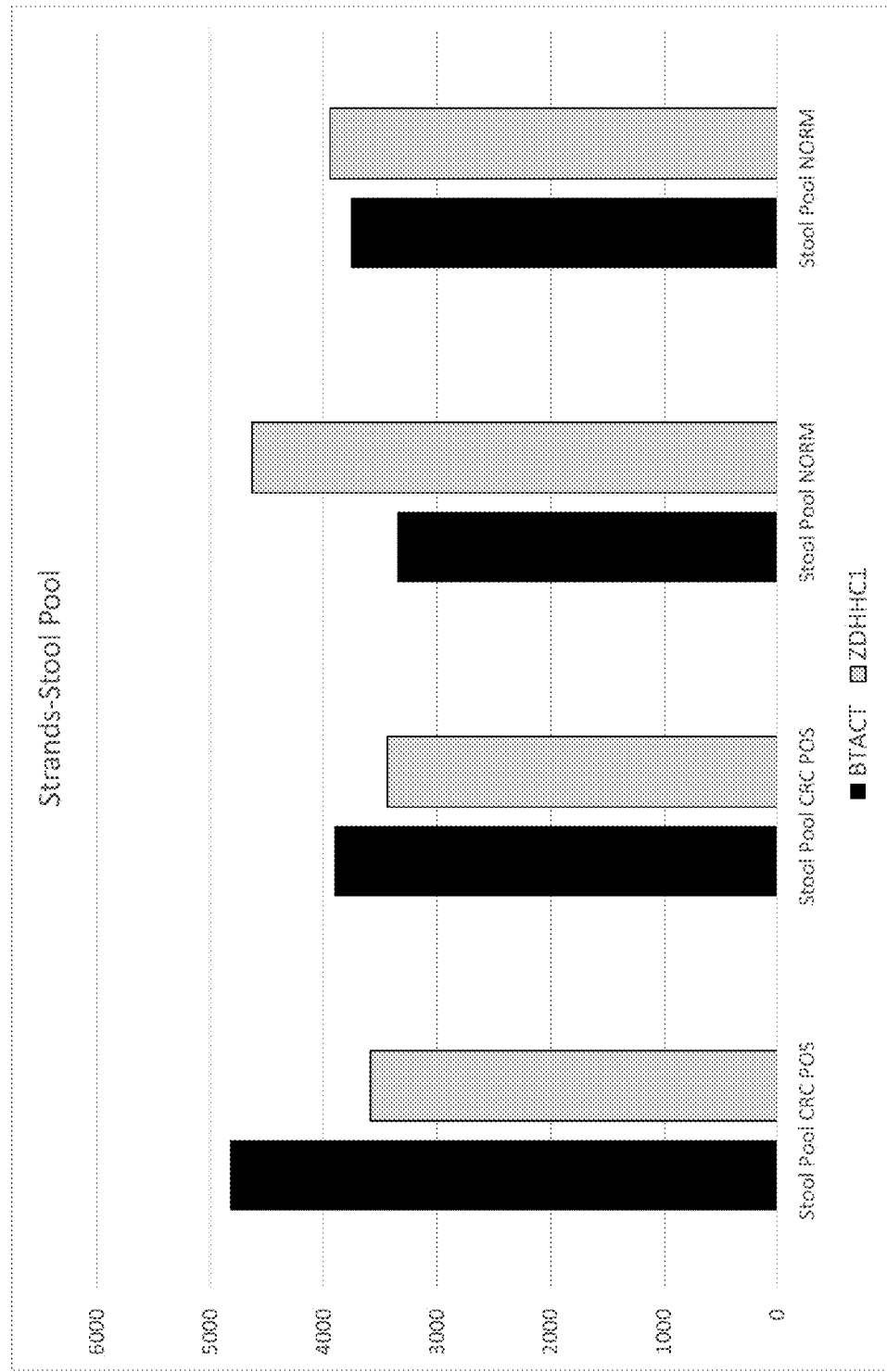
Figure 1D:
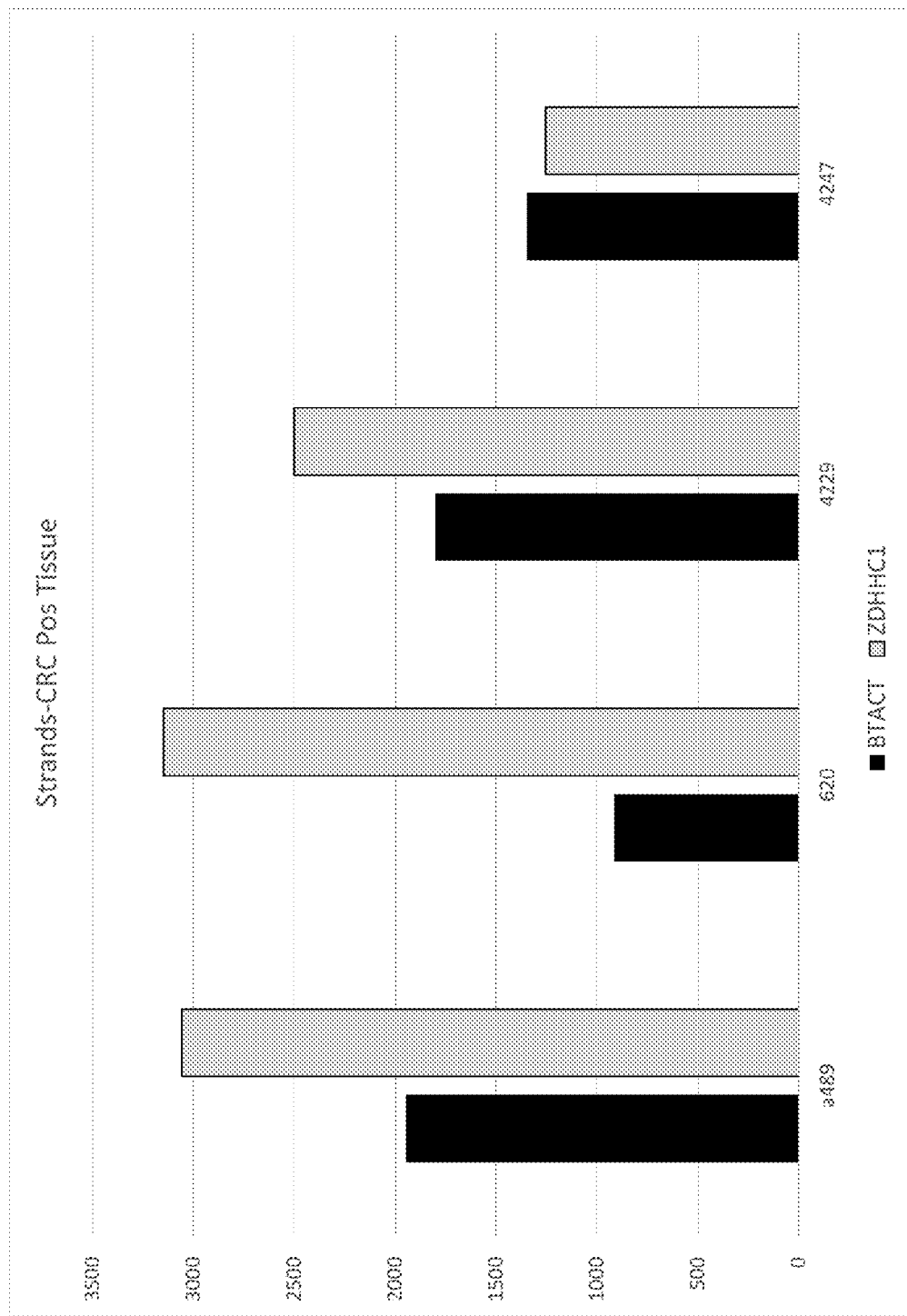
Figure 3A:
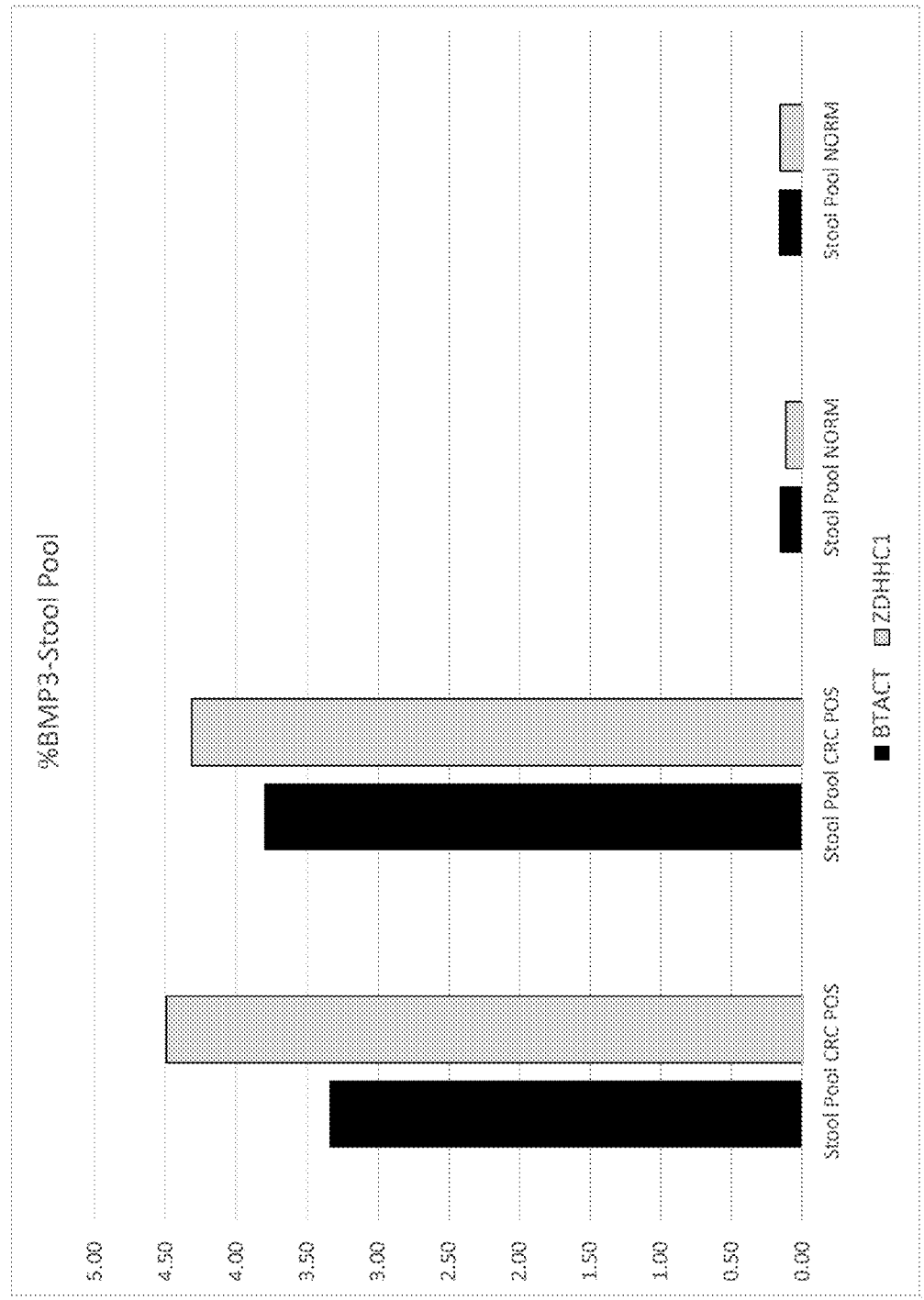
FIGS. 3A-3C provide graphs comparing the % methylation of marker gene BMP3 determined by comparison to control genes BTACT or ZDHHC1 in stool samples (3A), cell lines (3B) and colorectal cancer tissues samples (3C).
Figure 3B:
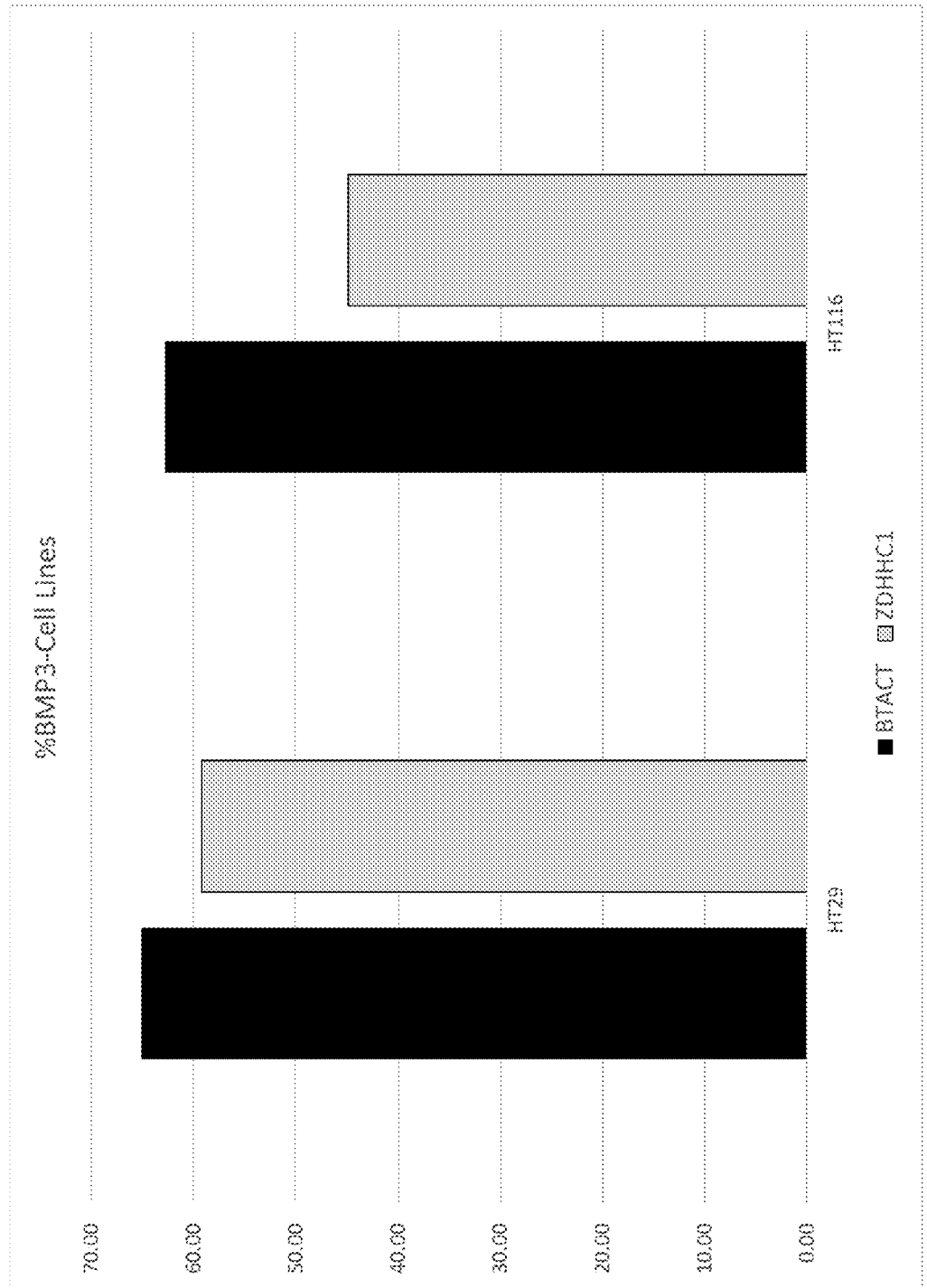
Figure 3C:
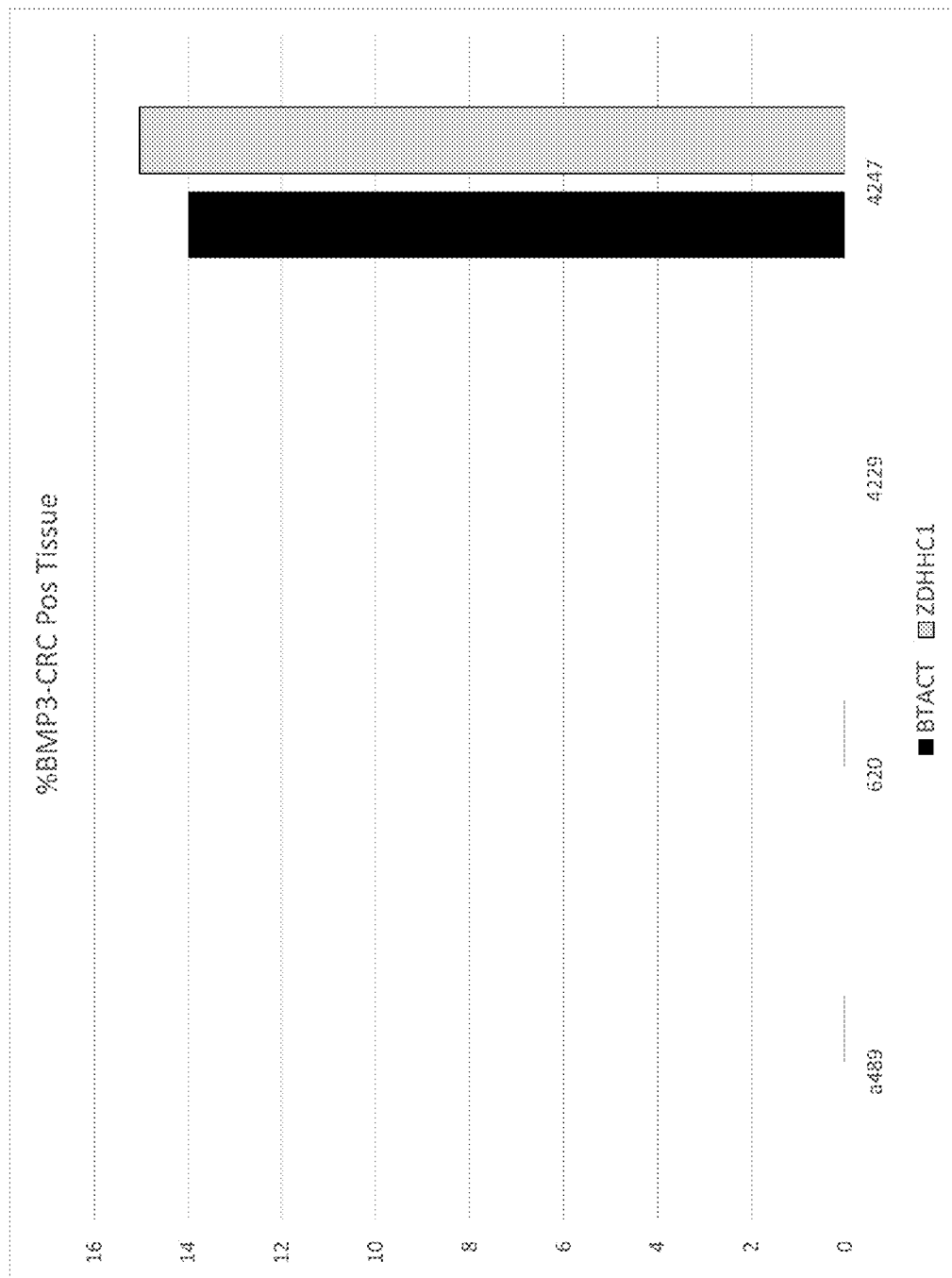

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the terms "subject" and "patient" refer to any animal, such as a dog, cat, bird, livestock, and particularly a mammal, preferably a human. In some instances, the subject is also a "user" (and thus the user is also the subject or patient).

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, crystals, and industrial samples. Such examples are not however to be construed as limiting the sample types applicable to the present invention.

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from a pancreas), the sample is a remote sample.

The term "target," when used in reference to a nucleic acid capture, detection, or analysis method, generally refers to a nucleic acid having a feature, e.g., a particular sequence of nucleotides to be detected or analyzed, e.g., in a sample suspected of containing the target nucleic acid. In some embodiments, a target is a nucleic acid having a particular sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

As used herein, the term "locus" refers to a particular position, e.g., of a mutation, polymorphism, or a C residue in a CpG dinucleotide, within a defined region or segment of nucleic acid, such as a gene or any other characterized sequence on a chromosome or RNA molecule. A locus is not limited to any particular size or length, and may refer to a portion of a chromosome, a gene, functional genetic element, or a single nucleotide or base pair. As used herein in reference to CpG sites that may be methylated, a locus refers to the C residue in the CpG dinucleotide.

As used herein, "a capture reagent" refers to any agent that is capable of binding to an analyte (e.g., a target). Preferably, "a capture reagent" refers to any agent that is capable of specifically binding to an analyte, e.g., having a higher binding affinity and/or specificity to the analyte than to any other moiety. Any moiety, such as a cell, a cellular organelle, an inorganic molecule, an organic molecule and a mixture or complex thereof can be used as a capture reagent if it has the requisite binding affinity and/or specificity to the analyte. The capture reagents can be peptides, proteins, e.g., antibodies or receptors, oligonucleotides, nucleic acids, vitamins, oligosaccharides, carbohydrates, lipids, small molecules, or a complex thereof. Capture reagents that comprise nucleic acids, e.g., oligonucleotides, may capture a nucleic acid target by sequence-specific hybridization (e.g., through the formation of conventional Watson-Crick basepairs), or through other binding interactions. When a capture oligonucleotide hybridizes to a target nucleic acid, hybridization may involve a portion of the oligonucleotide, or the complete oligonucleotide sequence, and the oligonucleotide may bind to a portion of or to the complete target nucleic acid sequence.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication US 20090253142 A1 (application Ser. No. 12/404,240), incorporated herein by reference in its entirety for all purposes. Additional amplification plus invasive cleavage detection configurations, termed the QuARTS method, are described in U.S. Pat. Nos. 8,361,720; 8,715,937; 8,916,344; and 9,127,318, incorporated herein by reference in their entireties for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above.

As used herein, the terms "complementary" or "complementarity" used in reference to polynucleotides (i.e., a sequence of nucleotides) refers to polynucleotides related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally, as in a purified restriction digest, or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like). The primer is typically single stranded for maximum efficiency in amplification, but may alternatively be partially or completely double stranded. The portion of the primer that hybridizes to a template nucleic acid is sufficiently long to prime the synthesis of extension products in the presence of the inducing agent. The exact lengths of the primers will depend on many factors, including temperature, source of primer and the use of the method. Primers may comprise labels, tags, capture moieties, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, amino acids, etc.) in the biopolymer. The sequence (e.g., base sequence) of a nucleic acid is typically read in the 5' to 3' direction.

As used herein, the term "gene" refers to a nucleic acid (e.g., DNA) sequence that comprises coding sequences necessary for the production of a polypeptide, precursor, or RNA (e.g., non-coding RNAs such as ribosomal RNA, transfer RNA, splicosomal RNA, microRNA). A polypeptide or non-coding RNA can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

The term "solid support" as used herein includes all the materials on which a target (e.g., DNA) can be immobilized. Natural or synthetic materials, which may or may not be chemically modified, can be used as a solid support, in particular polymers such as polyvinyl chloride, polyethylene, polystyrenes, polyacrylate or polyamide, or copolymers based on vinyl aromatic monomers, esters of unsaturated carboxylic acids, vinylidene chloride, dienes or compounds having nitrile functions (acrylonitrile); polymers of vinyl chloride and of propylene, polymers of vinyl chloride and vinyl acetate; copolymers based on styrenes or substituted derivatives of styrene; synthetic fibers, such as nylon; inorganic materials such as silica, glass, ceramic or quartz; latexes, magnetic particles; metal derivatives. Additional examples include, but are not limited to, a microtitration plate, a sheet, a cone, a tube, a well, beads (e.g., magnetic beads), particles or the like, or a flat support such as a silica or silicon wafer.

As used herein, the terms "magnetic particles" and "magnetic beads" are used interchangeably and refer to particles or beads that respond to a magnetic field. Typically, magnetic particles comprise materials that have no magnetic field but that form a magnetic dipole when exposed to a magnetic field, e.g., materials capable of being magnetized in the presence of a magnetic field but that are not themselves magnetic in the absence of such a field. The term "magnetic" as used in this context includes materials that are paramagnetic or superparamagnetic materials. The term "magnetic", as used herein, also encompasses temporarily magnetic materials, such as ferromagnetic or ferrimagnetic materials with low Curie temperatures, provided that such temporarily magnetic materials are paramagnetic in the temperature range at which silica magnetic particles containing such materials are used according to the present methods to isolate biological materials. The term "mixable" as used in reference to particles or beads refers to particles that are in free form, i.e., that are not immobilized, e.g., in a column, but that can be added to a sample and distributed in the sample fluid by mixing action (e.g., vortexing, stirring, shaking, repeated pipetting, etc.).

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

The term "highly methylated" refers to nucleic acids in which a particular locus (e.g., a CpG dinucleotide or set of dinucleotides or CpG-rich region) is methylated in a particular sample type or tissue type at a rate that is measurably greater than is observed for the comparable locus in the same DNA in another tissue or sample type. "Highly methylated" may refer to a single particular C-residue or to an average rate of methylation across multiple Cs in a region, as a fraction of the copies of that locus in the sample being assayed. Without limiting the term to any particular level of methylation, in some embodiments, a highly methylated locus may be >10% methylated, preferably >20% to 40%, more preferably >50% to 75%, still more preferably between 75% and 100%.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g., Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J Mol. Biol. 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) Proc. Natl. Acad. Sci. USA 97:

5237-5242; Salmon and Kaye (1970) *Biochim. Biophys. Acta.* 204: 340-351; Grafstrom (1985) *Nucleic Acids Res.* 13: 2827-2842; Nyce (1986) *Nucleic Acids Res.* 14: 4353-4367; Woodcock (1987) *Biochem. Biophys. Res. Commun.* 145: 888-894).

As used herein, the term "tissue cell" refers to any tissue cell in a body, e.g., a human or animal body, including, e.g., epithelium, muscle, nerve, and bone cells. Tissue cells do not include blood cells. As used herein, blood normally comprises plasma, red blood cells, white blood cells (including leukocytes and lymphocytes), and platelets. Leukocytes include neutophils, monocytes, eosinophils and basophils, and lymphocytes include T cells, B cells and natural killer cells.

"Tissue cell-specific control DNA" and "tissue cell-specific DNA refer to DNA that is detectable of the presence of tissue or in cell-free DNA from tissue, and that is minimally detectable or undetectable in blood or in a normal component of blood (e.g., plasma, white blood cells, etc., as listed above). As used herein, DNA that is methylated only in tissue and is not similarly methylated in blood (or vice versa) may be tissue-cell specific DNA with respect to the methylation state, even if the primary sequence of the DNA is the same in both cell types. "Epithelium-specific control DNA" refers to tissue-specific control DNA that detects DNA found in epithelial cells.

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) *Cancer Research* 57: 594-599.

The term "MethyLight™" refers to the art-recognized fluorescence-based real-time PCR technique described by Eads et al. (1999) *Cancer Res.* 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) *Nucleic Acids Res.* 25: 2529-2531.

The term "MSP" (Methylation-specific PCR) refers to the art-recognized methylation assay described by Herman et al. (1996) *Proc. Natl. Acad. Sci. USA* 93: 9821-9826, and by U.S. Pat. No. 5,786,146.

The term "COBRA" (Combined Bisulfite Restriction Analysis) refers to the art-recognized methylation assay described by Xiong & Laird (1997) *Nucleic Acids Res.* 25: 2532-2534.

The term "MCA" (Methylated CpG Island Amplification) refers to the methylation assay described by Toyota et al. (1999) *Cancer Res.* 59: 2307-12, and in WO 00/26401A1.

As used herein, the term "kit" refers to any delivery system for delivering materials. In the context of nucleic acid purification systems and reaction assays, such delivery systems include systems that allow for the storage, transport, or delivery of reagents and devices (e.g., inhibitor adsorbants, particles, denaturants, oligonucleotides, spin filters etc. in the appropriate containers) and/or supporting materials (e.g., buffers, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain materials for sample collection and a buffer, while a second container contains capture oligonucleotides and denaturant. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION

Provided herein is technology relating to performing assays for detection and quantification of DNA, e.g., methylated DNA. In particular, the technology relates to internal controls for such methylation assays.

Embodiments of the present disclosure provide a marker termed "ZDHHC1" for use as a methylation marker and internal control. Experiments conducted during the development of embodiments of the disclosure demonstrated that little or no methylated ZDHHC1 is found in normal blood samples (e.g., obtained from disease-free individuals). In contrast to commonly used internal control DNAs (e.g., β-actin), ZDHHC1 gives a very low background signal, e.g., from blood present in a tissue or stool sample. During development of the present technology, it was found that replacing the ACTB internal control with ZDHHC1 in an exemplary methylation assay (e.g. a flap endonuclease assay, such as a QUARTS assay) increased the sensitivity and specificity of the assay.

Further experiments demonstrated that ZDHHC1 serves as a marker that finds use in detecting epithelial tissue cells in blood (e.g., as a marker for metastatic cancer). Exemplary embodiments are described herein.

Although the disclosure herein refers to certain illustrated embodiments, it is to be understood that these embodiments are presented by way of example and not by way of limitation.

I. Tissue Cell—Specific Markers

In assays that detect and quantify methylated CpG-rich DNA that has undergone bisulfite conversion, it is typical to also detect a control gene present in the same sample, the control gene verifying the DNA input in the assay regardless of source (e.g., cancer, normal, stool, tissue). Such a control gene is used, for example, to normalize DNA copy number data obtained in assays across different samples, to accurately show higher or lower disease-associated marker levels sample-to-sample.

For a methylation assay normalizing gene to work best, it should meet several criteria. An ideal normalizing gene, for example: 1) should be equally present in both normal and diseased tissue; 2) should have approximately the same GC content as the test gene(s)/marker(s) that are being assayed (e.g., DNA markers in which hypermethylation is an indicator of a disease state); 3) should react in the same manner as the test genes/markers to pre-quantification (pre-PCR) sample treatments, such as bisulfite conversion; and 4) should have PCR amplification efficiency that is similar to that of the test genes/markers being assayed.

The β-actin gene, a gene typically used as a normalizing gene for detection of methylated marker DNAs, does not have the same GC content and CpG methylation as methylation markers associated with diseases such as cancer and adenoma (e.g., vimentin, septin 9, NDRG4, BMP3), so it does not behave like such marker DNAs in pre-PCR bisulfite conversion or in PCR amplification. In the development of the instant technology, it has been found that use of a normalizing gene that meets the criteria discussed above in place of ACTB improves assay sensitivity and specificity. In the development of the instant technology, it has further been found that use of a marker gene that is highly methylated in both normal and diseased tissue, but that is not methylated in blood provides a marker that is specific for tissue cells, e.g., epithelial cells, and that has a low presence in blood. Use of such control DNAs reduces background from any blood present in sample (e.g., a stool or tissue sample), and it also can be used to detect an abnormal presence of such tissue cells in blood, as may occur, e.g., during metastasis from a tumor.

Experiments described herein identified genes (e.g., ZDHHC1) that are highly methylated in normal and cancer tissue. These genes are not highly methylated in blood, and the degree to which they are methylated in blood does not change in accordance with a disease state, except as described in Example 6, in association with metastatic cancer. This allows for better and more accurate methylation calculation that is reflective of tissue only, and is independent of blood content in a sample. The genes described herein are used to normalize marker levels across patients and samples.

ZDHHC1, ZFAND3, ZMYM4, ODZ2, and TRIO were identified as candidate methylation markers. The selection of normalizing genes having low methylation in buffy coat allows for more sensitive detection of methylation of markers of interest (e.g., the denominator used for normalizing signal is low, and therefore, % methylation of the marker of interest becomes larger and easier to distinguish).

The normalizing genes described herein are highly methylated in tissue (cancer and normal) and are not highly methylated in blood, and provide several advantages over existing markers:
 1—GC-content and CpG methylation and bisulfite reactivity are more similar to the DNA marker(s) being studied.
 2—They display PCR amplification efficiency that is more similar to that of the marker DNA being measured.
 3—Low methylation state in buffy coat allows higher percent methylation detection of markers of interest in blood or in the presence of blood.

II. Methylation Detection Assays

The markers described herein (e.g., ZDHHC1 in particular), find use in a variety of methylation detection assays as normalization reagents and indicators of disease states.

The most frequently used method for analyzing a nucleic acid for the presence of 5-methylcytosine is based upon the bisulfite method described by Frommer, et al. for the detection of 5-methylcytosines in DNA (Frommer et al. (1992) *Proc. Natl. Acad. Sci. USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" *Clin Chem* 56: A199; U.S. Pat. No. 8,361,720, and U.S. patent application Ser. Nos. 12/946,745; 12/946,752, and 61/705,603).

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" *Nucleic Acids Res.* 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997) *Nucleic Acids Res.* 25: 2529-31; WO 95/00669; U.S. Pat. No. 6,251,594) to analyze individual cytosine positions. Some methods use enzymatic digestion (Xiong & Laird (1997) *Nucleic Acids Res.* 25: 2532-4). Detection by hybridization has also been described in the art (Olek et al., WO 99/28498). Additionally, use of the bisulfite technique for methylation detection with respect to individual genes has been described (Grigg & Clark (1994) *Bioessays* 16: 431-6; Zeschnigk et al. (1997) *Hum Mol Genet.* 6: 387-95; Feil et al. (1994) *Nucleic Acids Res.* 22: 695; Martin et al. (1995) *Gene* 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) *Proc. Natl. Acad. Sci. USA* 89: 1827-1831). Additionally, restriction enzyme digestion of PCR products amplified from bisulfite-converted DNA finds use in assessing methylation state, e.g., as described by Sadri & Hornsby (1997) *Nucl. Acids Res.* 24: 5058-5059 or as embodied in the method known as COBRA (Combined Bisulfite Restriction Analysis) (Xiong & Laird (1997) *Nucleic Acids Res.* 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase. The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components. Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" Nat Methods 7: 133-6; Meissner et al. (2005) "Reduced representation bisulfite sequencing for comparative high-resolution DNA methylation analysis" Nucleic Acids Res. 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199).

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

In some embodiments, the bisulfite-treated DNA is purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715, which is incorporated by reference in its entirety). In some embodiments, the bisulfite treated DNA is bound to a solid support, e.g., a magnetic bead, and desulfonation and washing occurs while the DNA is bound to the support. Examples of such embodiments are provided, e.g., in WO 2013/116375. In certain preferred embodiments, support-bound DNA is ready for a methylation assay immediately after desulfonation and washing on the support. In some embodiments, the desulfonated DNA is eluted from the support prior to assay.

In some embodiments, fragments of the treated DNA are amplified using sets of primer oligonucleotides according to the present invention (e.g., see Table 2) and an amplification enzyme. The amplification of several DNA segments can be carried out simultaneously in one and the same reaction vessel. Typically, the amplification is carried out using a polymerase chain reaction (PCR).

In another embodiment of the method, the methylation status of CpG positions within or near a marker are detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG. The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids", published as US 2012/0288868), incorporated herein by reference in its entirety.

In some embodiments, the markers described herein find use in QUARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer.

Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

Some biological samples, such as stool samples, contain a wide variety of different compounds that are inhibitory to PCR. Thus, the DNA extraction procedures include methods to remove and/or inactivate PCR inhibitors. As such, in some embodiments, processing and preparing samples and particularly, but not exclusively, to methods, systems, and kits for removing assay inhibitors from samples comprising nucleic acids are described in Example 1.

In some embodiments, the sample comprises blood, serum, plasma, gastric secretions, pancreatic juice, a gastrointestinal biopsy sample, microdissected cells from a gastrointestinal biopsy, gastrointestinal cells sloughed into the gastrointestinal lumen, and/or gastrointestinal cells recovered from stool. In some embodiments, the subject is human. These samples may originate from the upper gastrointestinal tract, the lower gastrointestinal tract, or comprise cells, tissues, and/or secretions from both the upper gastrointestinal tract and the lower gastrointestinal tract. The sample may include cells, secretions, or tissues from the liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

III. Other Applications

In some embodiments, diagnostic assays identify the presence of a disease or condition in an individual. In some embodiments, the disease is cancer (e.g., cancer of the gastrointestinal system).

The present disclosure is not limited to particular markers. In some embodiments, markers whose aberrant methylation is associated with a gastrointestinal neoplasm are utilized (e.g., one or more of vimentin, septin 9, NDRG4; see also U.S. Prov. Patent App. No. 62/091,053, filed Dec. 12, 2014, which is incorporated by reference herein in its entirety, for all purposes). In some embodiments, an assay further comprises detection of mutated KRAS genes (See e.g., Example 1). In some embodiments, assays further comprise detection of hemoglobin in stool samples (See e.g., Example 1).

In some embodiments, the technology relates to a method for treating a patient (e.g., a patient with gastrointestinal cancer, with early stage gastrointestinal cancer, or who may develop gastrointestinal cancer), the method comprising determining the methylation state of one or more markers as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing a gastrointestinal cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., those described herein), the methylation state of which is indicative of the presence, severity, or absence of the condition. Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., those described herein) disclosed herein. Further, in some embodiments of the presently disclosed subject matter, multiple determinations of the biomarkers over time can be made to facilitate diagnosis and/or prognosis. A temporal change in the biomarker can be used to predict a clinical outcome, monitor the progression of gastrointestinal cancer, and/or monitor the efficacy of appropriate therapies directed against the cancer. In such an embodiment for example, one might expect to see a change in the methylation state of one or more biomarkers disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with gastrointestinal cancer risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more target genes), the chance of a given outcome (e.g., suffering from a gastrointestinal cancer) may be very low. In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with a gastrointestinal cancer. In certain embodiments of the method, a subject is identified as having metaplasia upon identifying an aberrant methylation state of one or more markers provided herein in a biological sample obtained from the subject. In other embodiments of the method, the detection of an aberrant methylation state of one or more of such biomarkers in a biological sample obtained from the subject results in the subject being identified as having cancer.

In some embodiments, the subject is diagnosed as having a gastrointestinal cancer if, when compared to a control methylation state, there is a measurable difference in the methylation state of at least one biomarker in the sample. Conversely, when no change in methylation state is identified in the biological sample, the subject can be identified as not having gastrointestinal cancer, not being at risk for the cancer, or as having a low risk of the cancer. In this regard, subjects having the cancer or risk thereof can be differentiated from subjects having low to substantially no cancer or risk thereof. Those subjects having a risk of developing a gastrointestinal cancer can be placed on a more intensive and/or regular screening schedule, including endoscopic surveillance. On the other hand, those subjects having low to substantially no risk may avoid being subjected to an endoscopy, until such time as a future screening, for example, a screening conducted in accordance with the present technology, indicates that a risk of gastrointestinal cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, a gastrointestinal cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds, and horses. Thus, also provided is the diagnosis and treatment of livestock, including, but not limited to, domesticated swine, ruminants, ungulates, horses (including race horses), and the like. The presently-disclosed subject matter further includes a system for diagnosing a gastrointestinal cancer in a subject. The system can be provided, for example, as a commercial kit that can be used to screen for a risk of gastrointestinal cancer or diagnose a gastrointestinal cancer in a subject from whom a biological sample has been collected. An exemplary system provided in accordance with the present technology includes assessing the methylation state of a marker described herein.

Over recent years, it has become apparent that circulating epithelial cells, representing metastatic tumor cells, can be detected in the blood of many patients with cancer. Molecular profiling of rare cells is important in biological and clinical studies. Applications range from characterization of circulating epithelial cells (CEpCs) in the peripheral blood of cancer patients for disease prognosis and personalized treatment (See e.g., Cristofanilli M, et al. (2004) N Engl J Med 351:781-791; Hayes D F, et al. (2006) Clin Cancer Res 12:4218-4224; Budd G T, et al. (2006) Clin Cancer Res 12:6403-6409; Moreno J G, et al. (2005) Urology 65:713-718; Pantel et al., (2008) Nat Rev 8:329-340; and Cohen S J, et al. (2008) J Clin Oncol 26:3213-3221).

Experiments conducted during the course of development of embodiments of the present disclosure identified the unexpected result that the presence of methylated ZDHHC1 in blood or plasma is correlated with the presence of epithelial cells in blood in patients with metastatic cancer. Accordingly, embodiments of the present disclosure provide compositions and methods for detecting the presence of metastatic cancer in a subject by identifying the presence of methylated ZDHHC1 in plasma or whole blood. The presence of methylated ZDHHC1 is identified using any suitable method (e.g., those described herein).

EXPERIMENTAL EXAMPLES

Example 1

Methods for DNA Isolation and QUARTS Assay

The following provides exemplary method for DNA isolation prior to analysis, and an exemplary QUARTS assay, such as may be used in accordance with embodiments of the technology. Application of QuARTS technology to DNA from stool and various tissue samples is described in this example, but the technology is readily applied to other nucleic acid samples, e.g., as shown in other examples.
Collection of Target DNA from Stool Samples.

Whole stools are collected in plastic buckets. A preservative buffer, e.g., 150 mM EDTA, 500 mM Tris-Cl and 10 mM NaCl, (pH 9.0) is added to the stool, e.g., at about 4 ml per gram of stool, and buffered stools may be used directly or archived at −80° C.

Exemplary procedure for isolation of target nucleic acids from stool samples:
1. A stool sample is homogenized, e.g., with a buffer, to form a stool homogenate. The homogenate treated to partition residual solids from the fluid, e.g., by centrifugation or filtration, to produce a "stool supernatant."
2. Stool supernatant is treated to remove assay inhibitors (e.g., with polyvinylpolypyrrolidone, as described in U.S. Pat. No. 8,993,341, which is incorporated herein by reference in its entirety), producing "clarified supernatant".
3. Ten milliliters of clarified supernatant (representing an equivalent of approximately 4 grams of stool) is mixed with guanidine thiocyanate (GTC) to a final concentration of 2.4 M;
4. The mixture is then heated in a 90° C. water bath for 10 minutes to denature the DNA (and proteins) present in the stool.
5. Paramagnetic particles containing covalently attached (coupled) oligonucleotides complementary to the target sequence(s) of interest ("target-specific capture probes") are added to the sample. The sample is then incubated (e.g., at ambient temperature, about 22-25° C.) for one hour to enable hybridization of the target DNA to the capture probes on the magnetic particles.
6. The mixture of clarified supernatant, GTC, and particles is exposed to a magnetic field to separate the particles (now containing target DNA hybridized to the capture probes) from the stool supernatant/GTC mixture, which is transferred to a new tube.

See, e.g., U.S. patent application Ser. No. 13/089,116, which is incorporated herein by reference.

The denaturation/hybridization/separation cycle (steps 4-6) can be repeated, e.g., least four or more times to serially extract different target DNAs from the same stool supernatant sample.
FFPE Tissue DNA DNA from formalin-fixed, paraffin-embedded (FFPE) tissue is isolated using the QIAamp DNA FFPE Tissue Kit (Qiagen Sciences, Germantown, Md.).
DNA Isolation from Cells and Plasma For cell lines, genomic DNA may be isolated from cell conditioned media using, for example, the "Maxwell® RSC ccfDNA Plasma Kit (Promega Corp., Madison, Wis.). Following the kit protocol, 1 mL of cell conditioned media (CCM) is used in place of plasma, and processed according to the kit procedure.

An exemplary procedure for isolating DNA from a 4 mL sample of plasma is as follows:
To a 4 mL sample of plasma, 300 µL of Proteinase K (20 mg/mL) is added and mixed.
Add 3 µL of 1 µg/µL of Fish DNA to the plasma-proteinase K mixture.
Add 2 mL of plasma lysis buffer to plasma.
Plasma lysis buffer is:
4.3M guanidine thiocyanate
10% IGEPAL CA-630 (Octylphenoxy poly(ethyleneoxy)ethanol, branched)
(5.3 g of IGEPAL CA-630 combined with 45 mL of 4.8 M guanidine thiocyanate)
Incubate mixtures at 55° C. for 1 hour with shaking at 500 rpm.
Add 3 mL of plasma lysis buffer and mix.
Add 200 µL magnetic silica binding beads [16 µg of beads/µL] and mix again.
Add 2 mL of 100% isopropanol and mix.
Incubate at 30° C. for 30 minutes with shaking at 500 rpm.
Place tube(s) on magnet and let the beads collect. Aspirate and discard the supernatant.
Add 750 µL GuHCl-EtOH to vessel containing the binding beads and mix.
GuHCl-EtOH wash buffer is:
3M GuHCl
57%9 EtOH.
Shake at 400 rpm for 1 minute.
Transfer samples to a deep well plate or 2 mL microfuge tubes.

Place tubes on magnet and let the beads collect for 10 minutes. Aspirate and discard the supernatant.

Add 1000 µL wash buffer (10 mM Tris HCl, 80% EtOH) to the beads, and incubate at 30° C. for 3 minutes with shaking.

Place tubes on magnet and let the beads collect. Aspirate and discard the supernatant.

Add 500 µL wash buffer to the beads and incubate at 30° C. for 3 minutes with shaking.

Place tubes on magnet and let the beads collect. Aspirate and discard the supernatant.

Add 250 µL wash buffer and incubate at 30° C. for 3 minutes with shaking.

Place tubes on magnet and let the beads collect. Aspirate and discard the remaining buffer.

Add 250 µL wash buffer and incubate at 30° C. for 3 minutes with shaking.

Place tubes on magnet and let the beads collect. Aspirate and discard the remaining buffer.

Dry the beads at 70° C. for 15 minutes, with shaking.

Add 125 µL elution buffer (10 mM Tris HCl, pH 8.0, 0.1 mil EDTA) to the beads and incubate at 65° C. for 25 minutes with shaking.

Place tubes on magnet and let the beads collect for 10 minutes.

Aspirate and transfer the supernatant containing the DNA to a new vessel or tube.

QuARTS Assay

The QuARTS technology combines a polymerase-based target DNA amplification process with an invasive cleavage-based signal amplification process. The technology is described, e.g., in U.S. Pat. Nos. 8,361,720; 8,715,937; 8,916,344; and U.S. patent application Ser. No. 14/036,649, each of which is incorporated herein by reference. Fluorescence signal generated by the QuARTS reaction is monitored in a fashion similar to real-time PCR and permits quantitation of the amount of a target nucleic acid in a sample.

An exemplary QuARTS reaction typically comprises approximately 400-600 nmol/l (e.g., 500 nmol/l) of each primer and detection probe, approximately 100 nmol/l of the invasive oligonucleotide, approximately 600-700 nmol/l of each FRET cassette (FAM, e.g., as supplied commercially by Hologic, Inc.; HEX, e.g., as supplied commercially by BioSearch Technologies, IDT; and Quasar 670, e.g., as supplied commercially by BioSearch Technologies), 6.675 ng/µl FEN-1 endonuclease (e.g., Cleavase® 2.0, Hologic, Inc.), 1 unit Taq DNA polymerase in a 30 µl reaction volume (e.g., GoTaq® DNA polymerase, Promega Corp., Madison, Wis.), 10 mmol/l 3-(n-morpholino) propanesulfonic acid (MOPS), 7.5 mmol/l MgCl$_2$, and 250 µmol/l of each dNTP. Exemplary QuARTS cycling conditions consist of an initial incubation at 95° C. for 3 minutes, followed by 10 cycles of 95° C. for 20 seconds, 67° C. for 30 seconds, and 70° C. for 30 seconds. After completion of the 10 cycles, an additional 37 cycles at 95° C. for 20 seconds, 53° C. for 1 minute, 70° C. for 30 seconds, and 40° C. for 30 seconds are typically performed. In some applications, analysis of the quantification cycle ($C_q$) provides a measure of the initial number of target DNA strands (e.g., copy number) in the sample.

For stool DNA testing, capture probes are generally used as described above to capture target nucleic acid fragments from clarified supernatants, as discussed above. Examples of capture probes are shown below, and typically comprise a 5'-six carbon amino modified linkage (Integrated DNA Technology, Coralville, Iowa):

```
for NDRG4:
                                               (SEQ ID NO: 1)
/5AmMC6/TCCCTCGCGCGTGGCTTCCGCCTTCTGCGCGGCTGGGGTGCC
CGGTGG-3' for BMP3:
                                               (SEQ ID NO: 2)
/5AmMC6/GCGGGACACTCCGAAGGCGCAAGGAG-3' for KRAS:
                                               (SEQ ID NO: 3)
/5AmMC6/GGCCTGCTGAAAATGACTGAATATAAACTTGTGGTAGTTGGAG
C-3' and
                                               (SEQ ID NO: 4)
/5AmMC6/CTCTATTGTTGGATCATATTCGTCCACAAAATGATTCTGAATT
AGC-3'
```

Captured DNA for methylation testing is treated with bisulfite using, e.g., the EZ-96 DNA Methylation Kit (Zymo Research, Irvine Calif.) or using ammonium hydrogen sulfite as described in WO 2013/116375, incorporated herein by reference. The converted sample is typically eluted in 50 microliters of 10 mM Tris, 0.1 mM EDTA pH 8.0 with 20 nanograms per microliter tRNA (Sigma); 10 microliters of bisulfite-treated DNA are assayed with the QuARTS method in 30-microliter reaction volumes on a 96-well PCR plate. PCR plates are cycled in a LightCycler 480 (Roche).

QuARTS assays may be directed to individual markers or multiplexed combinations of markers, and typically additionally comprise oligonucleotides for detection of a reference nucleic acid, e.g., β-actin, or the markers discussed in embodiments of the invention, below.

In this embodiment, for each target below, the primers and probe (Integrated DNA Technology, Coralville, Iowa) are as follows:

```
for NDRG4:
                                               (SEQ ID NO: 5)
Primer     5'-CGG TTT TCG TTC GTT TTT TCG-3', (SEQ ID NO: 6)
Primer     5'-GTA ACT TCC GCC TTC TAC GC-3', (SEQ ID NO: 7)
Probe      5'-CGC CGA GGG TTC GTT TAT CG/3'C6/ for BMP3:
                                               (SEQ ID NO: 8)
Primer     5'-GTT TAA TTT TCG GTT TCG TCG TC-3'

(SEQ ID NO: 9)
Primer     5'-CTC CCG ACG TCG CTA CG-3'

(SEQ ID NO: 10)
Probe      5'-CGC CGA GGC GGT TTT TTG CG/3'C6/

For bisulfite-treated β-actin:
                                               (SEQ ID NO: 52)
Primer     5'-TTT GTT TTT TTG ATT AGG TGT TTA AGA-
           3'

(SEQ ID NO: 59)
Primer     5'-CAC CAA CCT CAT AAC CTT ATC-3'

(SEQ ID NO: 60)
Probe      5'-CCA CGG ACG ATA GTG TTG TGG/3'C6/
```

Each assay, e.g., in an assay plate, includes bisulfite-treated DNA samples, standard curve samples, positive and negative controls. Standard curves are may be made using target strands cut from engineered plasmids, e.g., at 300 to 1000 strands. Bisulfite-treated CpGenome universal methylated DNA (Millipore, Billerica, Mass.) and human genomic DNA (Merck, Germany) are used as positive and negative controls. DNA strand number is determined by comparing the $C_p$ of the target gene to the standard curve for the relevant assay. Percent methylation for each marker is determined by dividing the strand number of the methylated gene by the control DNA (e.g., β-actin, or the candidate control markers provided herein) strand number and multiplying by 100.

KRAS Mutations

QuARTS assays are used to evaluate seven mutations at codons 12/13 of the KRAS gene. Each mutation assay is designed as a singleplex assay. KRAS mutation-specific forward primers and probes are:

```
for G12S mutation:
                                        (SEQ ID NO: 11)
Primer   5'-CTT GTG GTA GTT GGA GCA A-3'

(SEQ ID NO: 12)
Probe    5'-GCG CGT CCA GTG GCG TAG GC/3'C6/;

for G12C mutation
                                        (SEQ ID NO: 13)
Primer   5'-AAA CTT GTG GTA GTT GGA CCT T-3'

(SEQ ID NO: 14)
Probe    5'-GCG CGT CCT GTG GCG TAG GC/3'C6/;

for G12R mutation
                                        (SEQ ID NO: 15)
Primer   5'-TAT AAA CTT GTG GTA GTT GGA CCT C-3'

(SEQ ID NO: 16)
Probe    5'-GCG CGT CCC GTG GCG TAG GC/3'C6/;

for G12D mutation
                                        (SEQ ID NO: 17)
Primer   5'-ACT TGT GGT AGT TGG AGC TCA-3'

(SEQ ID NO: 18)
Probe    5'-GCG CGT CCA TGG CGT AGG CA/3'C6/;

for G12V mutation
                                        (SEQ ID NO: 19)
Primer   5'-ACT TGT GGT AGT TGG AGC TCT-3'

(SEQ ID NO: 20)
Probe    5'-GCG CGT CCT TGG CGT AGG CA/3'C6/;

for G12A mutation
                                        (SEQ ID NO: 21)
Primer   5'-AAC TTG TGG TAG TTG GAG ATG C-3'

(SEQ ID NO: 22)
Probe    5'-GCG CGT CCC TGG CGT AGG CA/3'C6/;

for G13D mutation
                                        (SEQ ID NO: 23)
Primer   5'-GGT AGT TGG AGC TGG TCA-3'

(SEQ ID NO: 24)
Probe    5'-GCG CGT CCA CGT AGG CAA GA/3'C6/
```

For all KRAS mutants, the reverse primer used is

```
                                        (SEQ ID NO: 25)
5'-CTA TTG TTG GAT CAT ATT CGT C-3'
```

QuARTS cycling conditions and reagent concentrations for KRAS are the same as those in the methylation assays. Each plate contains standards made of engineered plasmids, positive and negative controls, and water blanks, and is run in a LightCycler 480 (Roche) or ABI 7500 (Thermo Scientific). DNA strand number is determined by comparing the $C_p$ or $C_T$ of the target gene to the standard curve for that assay. The concentration of each mutation marker in 50 microliters of KRAS is calculated based on the 500-fold dilution factor and an amplification efficiency of 1.95. This value is divided by the β-actin concentration or the ZDHH in the methylation assay and then multiplied by 100 to determine the percent mutation.

In the assays discussed below, "BTACT" refers to characterization of β-actin in the methylation assay and "ACT" or "ACTB" refers to characterization of β-actin in the mutation assay.

Example 2

Identification and Testing of Candidate Control Genes

As discussed above, in certain embodiments, control genes of the technology are selected according to methylation state. In a first step, genes that are highly methylated in both normal and cancer epithelial tissue cells are selected as candidate control genes. As a second step, the selected candidate genes are screened to identify genes wherein the methylated form of the gene is minimally present in blood and blood fractions. In preferred embodiments, candidate genes may be further analyzed to select genes having a GC-content and CpG methylation content similar to one or more marker gene(s) to be analyzed, such that bisulfite reactivity and PCR amplification behaviors are similar to the marker gene(s) to be analyzed.

ZDHHC1, ZFAND3, ZMYM4, ODZ2, and TRIO were identified as methylated genes possibly suitable for use as controls.

These candidate markers have the following loci (referenced to GRCh37/hg19 assembly):

ZDHHC1 footprint: Chr 16, 67428559-67428628
ZMYM4 footprint: Chr 1, 35877002-35877078
ZFAND3 footprint: Chr 6, 37841985-37842061
ODZ2 footprint: Chr 5, 167285650-167285775
TRIO footprint: Chr 5, 14461291-14461417

ZDHHC1, ZFAND3, and ZMYM4 genes were selected for further analysis and were assayed using QuARTS technology to compare methylation of the genes in the normal and cancer samples, and to assess presence of the markers in blood (e.g., in serum). The oligonucleotides used in the assays are shown schematically below. The term "wild type" is used to refer to the sequence of the genes in the absence of bisulfite conversion, which is not affected by methylation state.

```
ZDHHC1-zinc finger, DHHC-type containing 1
Untreated Target Sequence:
5'-GGGGCCGGGGCCGACAGCCCACGCTGGCGCGGCAGGCGCGTGCGCCCGCCGTTTTCGTGAGCCCGAGCAG-3'
(SEQ ID NO: 26)
```

-continued

Bisulfite-treated Target Sequence:
5'-GGGGUCGGGGUCGAUAGUUUACGUTGGCGCGGUAGGCGCGTGCGUUCGUCGTTTTCGTGAGUUCGAGUAG-3'
(SEQ ID NO: 33)

Bisulfite-treated, replicated Target Sequence:
5'-GGGGTCGGGGTCGATAGTTTACGTTGGCGCGGTAGGCGCGTGCGTTCGTCGTTTTCGTGAGTTCGAGTAG-3'
(SEQ ID NO: 27)

QuARTS Assay Design 1: (SEQ ID NO: 28)
```
            5' Arm-3-GTTGGCGCGGTA-3'
                     ||||||||||||            (SEQ ID NO: 27)
GGGGTCGGGGTCGATAGTTTACGTTGGCGCGGTAGGCGCGTGCGTTCGTCGTTTTCGTGAGTTCGAGTAG-3'
 ||||||||||||||||||||||                  ::::::::::::::::::::
5'-GTCGGGGTCGATAGTTTACG>>                 <<AGCAGCAAAAGCACTCAAGC-5'
     (SEQ ID NO: 29)                           (SEQ ID NO: 30)
```

QuARTS Assay Design 2 (v3):
```
                                      (SEQ ID NO: 31)
                                      GCACGCAAGCAG-Arm3-5'
       (SEQ ID NO: 27)                 ::::::::::::
GGGGTCGGGGTCGATAGTTTACGTTGGCGCGGTAGGCGCGTGCGTTCGTCGTTTTCGTGAGTTCGAGTAG
 ||||||||||||||||||||||                  ::::::::::::::::::::
    GTCGGGGTCGATAGTTTAGC>>                  <<GCAAAAGCACTCAAGCTCA
     (SEQ ID NO: 29)                           (SEQ ID NO: 32)
```

QuARTS Assay oligonucleotides (all shown 5' to 3'):
ZDHHC1 FP            GTCGGGGTCGATAGTTTACG                  SEQ ID NO: 29
ZDHHC1 RP            CGAACTCACGAAAACGACGA                  SEQ ID NO: 30
ZDHHC1 Probe A3      GACGCGGAG GTTGGCGCGGTA/3C6/           SEQ ID NO: 34
ZDHHC1 RP_v3         ACTCGAACTCACGAAAACG                   SEQ ID NO: 32
ZDHHC1 ProbeA3_v3    GACGCGGAG-GACGAACGCACG/3C6/           SEQ ID NO: 35
ZDHHC1 CP Prb        /5amm6/CTCGGGCTCACGAAAACGGCGGGCGCAC   SEQ ID NO: 36

ZFAND3-zinc finger, AN1-type domain 3
Untreated Target Sequence:
5'-TCTCTGTGTACTAATTTCCCTTTTTGGCCGGACGTGGTGGCTCACGCCTGTAATCCCAGCACTTTGGGAGGCCAAAG-3'
(SEQ ID NO: 37)

Bisulfite-treated Target Sequence:
5'-TTTTTGTGTATTAATTTTTTTTTTGGTCGGACGTGGTGGTTTACGTTTGTAATTTTAGTATTTTGGGAGGTTAAAG-3'
(SEQ ID NO: 38)

QuARTS Assay Design:         (SEQ ID NO: 39)
```
                  5'Arm-3-ACGTGGTGGTTT-3'
                           ||||||||||||          (SEQ ID NO: 38)
TTTTTGTGTATTAATTTTTTTTTTGGTCGGACGTGGTGGTTTACGTTTGTAATTTTAGTATTTTGGGAGGTTAAAG
 ||||||||||||||||||||||||||||              ::::::::::::::::::::::::::::
 5'-TGTGTATTAATTTTTTTTTTGGTCGG>>            <<TGCAAACATTAAAATCATAAAACCCTCC-5'
           (SEQ ID NO: 40)                          (SEQ ID NO: 41)
```

QuARTS Assay oligonucleotides (all shown 5' to 3'):
ZFAND3 FP            TGTGTATTAATTTTTTTTTTGGTCGGA             SEQ ID NO: 40
ZFAND3 RP            CCTCCCAAAATACTAAAATTACAAACGT            SEQ ID NO: 41
ZDAND3 Probe A3      GACGCGGAG ACGTGGTGGTTT /3C6/            SEQ ID NO: 42
ZFAND3 CP Prb        /5amm6/GTGCTGGGATTACAGGCGTGAGCCACCACGTCCGG  SEQ ID NO: 43

ZMYM4-zinc finger, MYM-type 4
Untreated Target Sequence:
5'-CCATCTATAGAAAAATGGATTAGGGCCGGGCACAGTGGCTCACGCCTGTAATCCCAGCACTTTGGGAGGCCGAGGCA-3'
(SEQ ID NO: 44)

Bisulfite-treated Target Sequence:
5'-TTATTTATAGAAAAATGGATTAGGGTCGGGTATAGTGGTTTACGTTTGTAATTTTAGTATTTTGGGAGGTCGAGGTA-3'
(SEQ ID NO: 45)

QuARTS Assay Design:              (SEQ ID NO: 46)
```
                         3'-CACCAAATGCAA-Arm-3-5'
                            ::::::::::::      (SEQ ID NO: 45)
TTATTTATAGAAAAATGGATTAGGGTCGGGTATAGTGGTTTACGTTTGTAATTTTAGTATTTTGGGAGGTCGAGGTA
         ||||||||||||||||||||||||              ::::::::::::::::::::::::::
         5'-GAAAAATGGATTAGGGTCGGGT>>            <<AACATTAAAATCATAAAACCCTCCAGCT-5'
              (SEQ ID NO: 47)                          (SEQ ID NO: 48)
```

```
-continued
QuARTS Assay oligonucleotide (all shown 5' to 3'):
ZMYM4 FP v2         GAAAAATGGATTAGGGTCGGGT                         SEQ ID NO: 47
ZMYM4 RP v2         TCGACCTCCCAAAATACTAAAATTACAA                   SEQ ID NO: 48
ZMYM4 Probe A3 v2   GACGCGGAG AACGTAAACCAC/3C6/                    SEQ ID NO: 49
ZMYM4 CP Prb        /5amm6/CGGCCTCCCAAAGTGCTGGGATTACAGGCGTGAGCC    SEQ ID NO: 50

Quasar 670 A3 FRET Cassette:
5' d Q670-TCT(I-BHQ2)AGCCGGTTTTCCGGCTGAGACTCCGCGTC-C6 3'
(SEQ ID NO: 51)

[FP = forward primer; RP = reverse primer; 3' C6 = 3' hexane; 5amm6 = 5' amino;
CP = capture probe; Q670 = Quasar ® 670 dye; BHQ2 = Black Hole Quencher 2]
```

Using the oligonucleotide combinations described above, methylation analysis of cancer markers NDRG4 and BMP3 was performed on a variety of different sample types (blood, plasma, and two human colorectal cancer cell lines, HT29 and HT116) using β-actin (BTACT) for normalization, or using one of the three candidate control genes (ZDHHC1, ZMYM, and ZFAND) for normalization. Assays were performed in duplicate as described in Example 1. Table 1 shows the averages of the replicates:

TABLE 1

| | Average Strands | | | | | |
|---|---|---|---|---|---|---|
| SampleID | NDRG4 | BMP3 | BTACT | ZDHHC1 | ZFAND3 | ZMYM4v2 |
| Blood | 0 | 8 | 18160 | 0 | 41136 | 42905175 |
| Plasma | 0 | 0 | 1 | 0 | 15 | 9382 |
| HT29 | 66008 | 64728 | 114720 | 141602 | 106223 | 36106311 |
| HT116 | 75394 | 59933 | 114944 | 257075 | 112873 | 35033276 |

It can be seen from these data that all three candidate markers, like BTACT, show strong positive signal in cancer cell lines HT29 and HT116. However, both ZFAND3 and ZMYM4v2, like BTACT, show significant signal in blood samples, such as can produce undesirable background in samples having an amount of blood present, e.g., tissue or stool samples.

This example shows that ZDHHC1 has lower background signal in blood and plasma, and that it is readily detected in epithelial cell lines. ZDHHC1 was selected for further analysis.

Example 3

Comparing β-Actin and ZDHHC1 for Normalizing Cancer Marker Assays

The ZDHHC1 marker was tested in parallel with BTACT, to compare these DNAs as controls for determining % methylation of the NDRG4 and BMP3 marker genes. DNA isolated from formalin-fixed, paraffin-embedded tissue samples was characterized, with assay signals normalized to β-actin or ZDHHC1. The results are shown in Table 3, below.

These data show that % methylation of the NDRG4 and BMP3 markers relative to ZDHHC1 is comparable to % methylation of the same markers relative to β-actin, showing that ZDHHC1 may be used in place of β-actin for normalizing.

TABLE 3

| | Strands normalized to ZDHHC1 | | | % Methylation relative to ZDHHC1 | | Strands normalized to BTACT | | | % Methylation relative to BTACT | |
|---|---|---|---|---|---|---|---|---|---|---|
| SampleID | NDRG4 | BMP3 | ZDHHC1 | % NDRG4 | % BMP3 | NDRG4 | BMP3 | BTACT | % NDRG4 | % BMP3 |
| 683 (1:5) | 31 | 0 | 123 | 25.5 | 0.0 | 99 | 0 | 356 | 27.8 | 0.0 |
| 538 (1:5) | 625 | 504 | 563 | 111.0 | 89.4 | 2413 | 1559 | 3739 | 64.5 | 41.7 |
| 536 (1:5) | 1126 | 0 | 1105 | 101.9 | 0.0 | 3737 | 0 | 3421 | 109.2 | 0.0 |
| 279 (1:5) | 365 | 518 | 899 | 40.6 | 57.6 | 3935 | 4671 | 11449 | 34.4 | 40.8 |

TABLE 3-continued

| | Strands normalized to ZDHHC1 | | | % Methylation relative to ZDHHC1 | | Strands normalized to BTACT | | | % Methylation relative to BTACT | |
|---|---|---|---|---|---|---|---|---|---|---|
| SampleID | NDRG4 | BMP3 | ZDHHC1 | % NDRG4 | % BMP3 | NDRG4 | BMP3 | BTACT | % NDRG4 | % BMP3 |
| 544 (1:5) | 4739 | 1159 | 3684 | 128.6 | 31.5 | 44858 | 17705 | 41324 | 108.6 | 42.8 |
| 602 (1:5) | 238 | 22 | 5533 | 4.3 | 0.4 | 3784 | 163 | 67690 | 5.6 | 0.2 |
| 654 (1:5) | 43 | 4 | 1067 | 4.0 | 0.4 | 965 | 25 | 20833 | 4.6 | 0.1 |
| 686 (1:5) | 198 | 168 | 985 | 20.1 | 17.1 | 1077 | 1140 | 1957 | 55.0 | 58.3 |
| 160 (1:5) | 1347 | 784 | 2095 | 64.3 | 37.4 | 45346 | 36657 | 85629 | 53.0 | 42.8 |
| 309 (1:5) | 0 | 3 | 7039 | 0.0 | 0.0 | 0 | 8 | 65247 | 0.0 | 0.0 |
| 602 (1:5) | 130 | 19 | 3133 | 4.2 | 0.6 | 3784 | 163 | 67690 | 5.6 | 0.2 |
| 131 | 66 | 41 | 135 | 49.2 | 30.5 | 169 | 92 | 336 | 50.3 | 27.4 |
| 669 | 167 | 201 | 592 | 28.2 | 34.0 | 271 | 235 | 744 | 36.4 | 31.6 |
| 681 | 932 | 815 | 567 | 164.4 | 143.7 | 822 | 745 | 464 | 177.2 | 160.6 |
| 673 | 0 | 0 | 171 | 0.0 | 0.0 | 0 | 0 | 145 | 0.0 | 0.0 |

As shown in Table 3, comparison of the % methylation values determined using ZDHHC1 and using BTACT shows that these controls are equivalent in performance on these tissue samples, and that ZDHHC1 may be used in place of BTACT in measuring methylation of the cancer marker genes.

Example 4

ZDHHC1 and β-Actin DNA in Normal and Cancer Tissue Samples

This example describes a comparison of the number of ZDHHC1 and β-actin strands in an extended sampling of different cancerous and normal tissue samples. DNA from normal and abnormal tissue types, including bile duct, colon, esophageal, head, lung, pancreas, small bowel, and stomach, were tested.

DNA isolated from formalin-fixed, paraffin-embedded tissue samples was characterized, with median assay signals for β-actin (ACTB) and ZDHHC1 shown in Table 4, below.

TABLE 4

| Tissue/disease | Median (ZDHHC1 strands) | Median (ACTB strands (WT)) |
|---|---|---|
| Bile duct/ACA | 2500.5 | 7470 |
| Bile duct/normal | 2516.5 | 12300 |
| Colon/ACA | 1229.5 | 32883.5 |
| Colon/adenoma-ge-1cm | 865 | 20409.5 |
| Colon/HGD | 1423 | 15210 |
| Colon/normal | 355.5 | 7666 |
| Colon/SSP | 1255.5 | 11268 |
| Esophagus/cancer | 506 | |
| Esophagus/normal | 648 | |
| Esophagus/adenocarcinoma | 735 | 4760 |
| Esophagus/SCC | 1258 | 20950 |
| Head/oropharyng. | 279 | 23158.5 |
| Lung/large airway | 201 | 4330 |
| Pancreas/ACA | 1345 | |
| Pancreas/normal | 1397.5 | |
| Small bowel/ACA | 609.5 | 17767 |
| Small bowel/adenoma | 543 | 11936.5 |
| Stomach/ACA | 642 | 14826 |
| Stomach/adenoma | 465 | 20164 |
| Stomach/metaplasia | 1238 | 10695 |
| Stomach/normal | 220.5 | 10555.5 |

These data confirm that the methylated ZDHHC1 control is detected in all tissue types tested, and in normal and non-normal (e.g., adenoma, carcinoma, metaplasia) tissue types. Results show equal ZDHHC1 methylation between cancer and normal tissues.

Example 5

Effect of ZDHHC1 for Normalizing Cancer Marker Assays in Complex Samples

Further experiments were conducted on the use of ZDHHC1 as a normalizing marker in assays to detect cancer in more complex samples, e.g., stool, blood, etc., and in normal and colorectal cancer tissue samples. Table 5A shows the strands detected of the NDRG4 methylation marker and for both control DNAs, and shows the % methylation of NDRG4 as determined using each control DNA. Data for the BMP3 marker detected in the same assay reactions in shown in Table 5B.

TABLE 5A

| | Marker Gene Strands | Control Gene Strands | | % NDRG4 Methylation calculated from each control DNA | |
|---|---|---|---|---|---|
| Sample ID | NDRG4 | BTACT | ZDHHC1 | BTACT | ZDHHC1 |
| Stool Pool CRC POS | 596 | 4825 | 3589 | 12.35 | 16.61 |
| Stool Pool CRC POS | 569 | 3906 | 3441 | 14.56 | 16.53 |
| Stool Pool NORM | 25 | 3349 | 4630 | 0.74 | 0.53 |
| Stool Pool NORM | 32 | 3762 | 3943 | 0.85 | 0.81 |
| Blood | 0 | 16036 | 16 | 0 | 0 |
| Blood | 0 | 17970 | 0 | 0 | 0 |
| Cell Lines | | | | | |
| HT29 | 73418 | 111915 | 123115 | 65.60 | 59.63 |
| HT116 | 84758 | 106098 | 148448 | 79.89 | 57.10 |
| Colorectal Cancer Positive Tissue Samples | | | | | |
| a489 | 855 | 1946 | 3057 | 43.91 | 27.96 |
| 620 | 334 | 913 | 3148 | 36.55 | 10.60 |
| 4229 | 0 | 1801 | 2502 | 0 | 0 |
| 4247 | 278 | 1347 | 1255 | 20.65 | 22.17 |
| Normal Tissue Samples | | | | | |
| 1233402220 | 0 | 1398 | 1772 | 0 | 0 |
| 1233402240 | 0 | 1065 | 1811 | 0 | 0 |
| 1233402253 | 0 | 1227 | 1859 | 0 | 0 |

TABLE 5B

| Sample ID | Marker Gene Strands BMP3 | Control Gene Strands BTACT | Control Gene Strands ZDHHC1 | % BMP3 Methylation calculated from each control DNA BTACT | % BMP3 Methylation calculated from each control DNA ZDHHC1 |
|---|---|---|---|---|---|
| Stool Pool CRC POS | 161 | 4825 | 3589 | 3.34 | 4.49 |
| Stool Pool CRC POS | 149 | 3906 | 3441 | 3.80 | 4.32 |
| Stool Pool NORM | 5 | 3349 | 4630 | 0.16 | 0.12 |
| Stool Pool NORM | 6 | 3762 | 3943 | 0.17 | 0.16 |
| Blood | 2 | 16036 | 16 | 0.01 | 9.71 |
| Blood | 1 | 17970 | 0 | 0.01 | 0 |
| Cell Lines | | | | | |
| HT29 | 72886 | 111915 | 123115 | 65.13 | 59.20 |
| HT116 | 66605 | 106098 | 148448 | 62.78 | 44.87 |
| Colorectal Cancer Positive Tissue Samples | | | | | |
| a489 | 0 | 1946 | 3057 | 0 | 0 |
| 620 | 0 | 913 | 3148 | 0 | 0 |
| 4229 | 0 | 1801 | 2502 | 0 | 0 |
| 4247 | 189 | 1347 | 1255 | 14.00 | 15.03 |
| Normal Tissue Samples | | | | | |
| 1233402220 | 0 | 1398 | 1772 | 0.03 | 0.02 |
| 1233402240 | 1 | 1065 | 1811 | 0.05 | 0.03 |
| 1233402253 | 0 | 1227 | 1859 | 0 | 0 |

These data show that the methylated ZDHHC1 control DNA presence is essentially uniform in stool samples from both normal and colorectal cancer-positive subjects, and confirm that the marker is substantially absent in blood samples. These data also confirm that ZDHHC1 presence is essentially equivalent to β-actin DNA samples that do not contain blood (e.g., cell lines).

Example 6

ZDHHC1 in Plasma Samples of Subjects with Metastatic Cancer

This example described detection of ZDHHC1 in plasma samples of patients with metastatic cancer.

One to two milliliter samples of normal, advanced adenoma (AA) and adenocarcinoma (ACA), patient plasma were used in QUARTS assays. Plasma samples from colon cancer subjects and normal subjects were processed using Qiagen Circulating Nucleic Acid Kit. Starting volumes of plasma ranged from 0.75-2.0 ml. DNA was bisulfite-converted and tested with ZDHHC1 and the BTACT oligo mixtures. Results show that ZDHHC1 strand levels were high in the stage IV cancer sample with liver metastasis.

All samples, except one, had no ZDHHC1 marker strands. The one sample that showed large number of strands for ZDHHC1 marker in plasma is a stage IV metastases. These data support the use of ZDHHC1 to detect epithelial cells in blood/plasma as a general marker for metastasis. Results are summarized in the Table 6:

TABLE 6

| Type | Number | Avg. BTACT strands | Avg. ZDHHC strands | Avg. Z/BTACT % |
|---|---|---|---|---|
| Normal | 8 | 481 | 4 | 1 |
| AA | 4 | 193 | 3 | 2 |
| ACA, stage I* | 3 | 104 | 1 | 1 |
| ACA, stage II | 6 | 264 | 6 | 2.3 |
| ACA, stage III | 2 | 200 | 10 | 50 |
| ACA, stage IV, w/mets | 1 | 2325 | 3998 | 172 |

*includes one sample not characterized by stage.

In an additional study of two AA samples, eight ACA samples, of which two were classed as stage IV with observed metastases, and 34 normal samples, one of the stage IV was detected, displaying a significantly elevated ratio of ZDHHC1/BTACT (41%) and one appeared to have normal ratio of ZDHHC1/BTACT (4.3%). None of the other samples displayed an elevated ratio of ZDHHC1/BTACT.

Example 7

ZDHHC1 in Plasma Samples of Subjects with Cancer

Plasma levels for ZDHHC1 were measured on an additional set of patient samples comprising 57 samples from patients with cancer and 52 normal samples, as detailed in FIGS. 4A-4E. DNA was extracted from 4 ml of plasma and bisulfite-converted. The ZDHHC1 DNA was pre-amplified for 10 cycles then detected using a QuARTS flap assay as described in Example 1, using the primers and probes described in Example 2. The results are shown in the table in FIGS. 4A-4E, and the averaged data for each sample type is as follows:

| Sample | Diagnosis | ZDHHC1 copies |
|---|---|---|
| Plasma | Normal Colonoscopy | Avg Copies = 11 |
| Plasma | Panc Cancer | Avg Copies = 1,041 |
| Plasma | Small Bowel Cancer | Avg Copies = 12,001 (1 Sample) |
| Plasma | Lung Cancer | Avg Copies = 300 |
| Plasma | Colorectal Cancer | Avg Copies = 459 |

Example 8

Detection of ZDHHC1 for Monitoring Disease State and/or Progression

Patient samples, e.g., blood product samples such as plasma samples, may be analyzed for the presence of epithelial cells or epithelial cell DNA as means of monitoring a disease state, e.g., occurrence, progression, response to therapy, post-surgery, remission, recurrence, etc. In some embodiments, samples are taken from a patient at multiple time points and the amount of ZDHHC1 DNA present (whether free or in circulating cells or complexes) is measured at each time point, and the amounts of ZDHHC1 DNA in the samples taken at the different time points are compared to assess changes in the disease state.

At a first time point, a sample of blood is taken from a patient and a plasma sample is prepared.

At a second time point, a second sample of blood is taken from the patient and a second plasma sample is prepared.

Either the entire blood sample is tested for ZDHHC1 DNA or the sample is further processed to yield a plasma fraction.

Each plasma sample is tested for the presence and amount of ZDHHC1 DNA, e.g., using methods as described in Example 1 and 6, above. It is contemplated that, in some embodiments, the first sample is not immediately tested (e.g., the blood or the plasma, or DNA isolated therefrom, is stored for later testing) and the first and second samples are tested at the same time. In other embodiments, the first plasma sample is tested prior to the collection of the second blood sample, and the results are stored for later comparison.

The technology is not limited to a particular event or course of action occurring between the first and second time points. For example, the first time point may be at a time where there is no suspicion of disease, e.g., the first assay may be to establish a baseline in the expectation of monitoring the subject for future disease occurrence. Alternatively, the first time point may be taken at a point at which a condition or disease may be present in the subject, but the disease state is one for which monitoring is preferred over active therapeutic intervention as a course of action, e.g., the disease state may be monitored for changes such as metastases. In other situations, active therapy, e.g., surgery, drug therapy, etc., may be administered to the subject between the two time points, and the measurement of epithelial cell DNA in the blood may be used to monitor efficacy of the therapy.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method of characterizing blood or blood product, comprising:
   a) providing a blood or blood product sample from a subject;
   b) assaying said sample to detect the presence of ZDHHC1 epithelial cell-specific DNA,
   wherein said assaying comprises:
      i) treating DNA from said sample with a bisulfite reagent to create bisulfite-converted ZDHHC1 DNA comprising the nucleotide sequence of SEQ ID NO:33;
      ii) amplifying a region of said bisulfite converted DNA using a pair of primers complementary to primer binding sites within SEQ ID NO:27 and its complement, wherein in said amplifying, said primers hybridize to said primer binding sites and are extended to amplify a region of SEQ ID NO:27 bounded by the primer binding sites to produce amplified product; and
      iii) detecting said amplified product.

2. The method of claim 1, wherein said blood product is plasma.

3. The method of claim 1, wherein said detecting comprises detecting hybridization of the amplified product to a detection probe.

4. The method of claim 3, wherein said detection probe comprises a reporter molecule.

5. The method of claim 4, where said reporter molecule comprises a fluorophore.

6. The method of claim 3, wherein said detection probe comprises a flap sequence.

7. The method of claim 3, wherein said detecting hybridization of the amplified product to said detection probe comprises use of a FRET cassette.

8. The method of claim 3, wherein said detecting hybridization of the amplified product to said detection probe comprises use of a FEN-1 endonuclease.

9. The method of claim 1, wherein assaying said sample comprises measuring an amount of ZDHHC1 epithelial cell-specific DNA in the blood or blood product sample.

10. The method of claim 9, wherein said measuring comprises a quantitative amplification reaction.

11. The method of claim 10, wherein the quantitative amplification reaction comprises real-time fluorescence detection.

* * * * *